(12) United States Patent
Tsai

(10) Patent No.: US 11,524,147 B2
(45) Date of Patent: Dec. 13, 2022

(54) VALVE SYSTEM FOR INFLATABLE DEVICES

(71) Applicant: CONVATEC TECHNOLOGIES INC., Las Vegas, NV (US)

(72) Inventor: Mingliang Lawrence Tsai, Holmdel, NJ (US)

(73) Assignee: CONVATEC TECHNOLOGIES, INC., Las Vegas, NV (US)

( * ) Notice: Subject to any disclaimer, the term of this patent is extended or adjusted under 35 U.S.C. 154(b) by 0 days.

(21) Appl. No.: 17/071,342

(22) Filed: Oct. 15, 2020

(65) Prior Publication Data

US 2021/0038870 A1 Feb. 11, 2021

Related U.S. Application Data

(62) Division of application No. 15/772,020, filed as application No. PCT/US2016/059132 on Oct. 27, 2016, now Pat. No. 10,842,976.

(Continued)

(51) Int. Cl.

| | |
|---|---|
| *A61M 25/10* | (2013.01) |
| *A61M 25/00* | (2006.01) |
| *A61M 16/04* | (2006.01) |
| *A61F 5/00* | (2006.01) |
| *A61F 5/44* | (2006.01) |

(Continued)

(52) U.S. Cl.
CPC ..... *A61M 25/10186* (2013.11); *A61F 5/0093* (2013.01); *A61F 5/4405* (2013.01); *A61F 5/451* (2013.01); *A61M 16/044* (2013.01); *A61M 25/0017* (2013.01); *A61M 25/10187* (2013.11); *A61F 2005/4455* (2013.01);

(Continued)

(58) Field of Classification Search
CPC ...... A61M 25/10186; A61M 25/10187; A61M 16/044; A61M 25/0017; A61M 2210/1064; A61F 5/0093; A61F 5/4405; A61F 5/451; A61F 2005/4455; Y10T 137/36; Y10T 137/7779
USPC ........................................ 604/99.02
See application file for complete search history.

(56) References Cited

U.S. PATENT DOCUMENTS

| | | | | |
|---|---|---|---|---|
| 851,530 | A | ‡ | 4/1907 | Lamport ................. A61M 3/00 604/99 |
| 2,254,997 | A | ‡ | 9/1941 | Fisher .................... F16L 29/04 137/61 |

(Continued)

FOREIGN PATENT DOCUMENTS

| | | |
|---|---|---|
| CN | 104105524 A | 10/2014 |
| CN | 105407961 A ‡ | 3/2016 |

(Continued)

OTHER PUBLICATIONS

Examination Report No. 1 for Standard Patent Application; Australian Government; IP Australia; Australian Patent Application No. 2016344123; dated Sep. 8, 2020; 5 pages.‡

(Continued)

*Primary Examiner* — Andrew J Mensh
(74) *Attorney, Agent, or Firm* — Taft Stettinius & Hollister LLP; Ryan O. White; Derek B. Lavender

(57) ABSTRACT

Valves and valve systems are provided that are useful for integration with inflatable indwelling medical devices to prevent over-inflation of retention balloon.

24 Claims, 11 Drawing Sheets

Related U.S. Application Data

(60) Provisional application No. 62/247,934, filed on Oct. 29, 2015.

(51) Int. Cl.
*A61F 5/451* (2006.01)
*A61F 5/445* (2006.01)

(52) U.S. Cl.
CPC .... *A61M 2210/1064* (2013.01); *Y10T 137/36* (2015.04); *Y10T 137/7779* (2015.04)

(56) References Cited

U.S. PATENT DOCUMENTS

| | | | | |
|---|---|---|---|---|
| 2,845,930 A ‡ | 8/1958 | Brown | A61M 25/00 | 600/560 |
| 3,127,148 A ‡ | 3/1964 | Collar | F16L 37/22 | 251/14 |
| 3,211,150 A * | 10/1965 | Foderick | A61M 25/10185 | 604/97.02 |
| 3,446,245 A ‡ | 5/1969 | Snyder, Jr. | F16L 37/32 | 137/61 |
| 3,721,726 A ‡ | 3/1973 | Schwartzman | A61M 35/003 | 264/24 |
| 3,777,757 A ‡ | 12/1973 | Gray | A61M 25/1011 | 604/99 |
| 4,102,342 A ‡ | 7/1978 | Akiyama | A61M 25/10183 | 606/192 |
| 4,116,201 A * | 9/1978 | Shah | A61M 25/10185 | 128/207.15 |
| 4,178,938 A ‡ | 12/1979 | Au | A61M 39/22 | 128/20 |
| 4,185,638 A ‡ | 1/1980 | Bruner | A61M 25/10183 | 604/100.01 |
| 4,280,498 A ‡ | 7/1981 | Jensen | A61F 5/4405 | 251/31 |
| 4,431,019 A ‡ | 2/1984 | Kopp | G05D 11/003 | 137/87 |
| 4,541,457 A ‡ | 9/1985 | Blenkush | F16L 37/0841 | 137/61 |
| 4,629,159 A ‡ | 12/1986 | Wellenstam | A61M 39/26 | 251/14 |
| 4,948,092 A ‡ | 8/1990 | Kasper | F16K 15/147 | 137/22 |
| 4,955,879 A ‡ | 9/1990 | Mervine | A61F 5/44 | 604/31 |
| 5,350,364 A ‡ | 9/1994 | Stephens | A61M 39/06 | 604/16 |
| 5,454,784 A ‡ | 10/1995 | Atkinson | A61M 3/0216 | 604/31 |
| 5,496,300 A ‡ | 3/1996 | Hirsch | A61F 5/4404 | 137/61 |
| 5,609,195 A ‡ | 3/1997 | Stricklin | F16L 37/28 | 141/34 |
| 5,628,726 A ‡ | 5/1997 | Cotter | A61M 39/14 | 137/61 |
| 5,709,244 A ‡ | 1/1998 | Patriquin | F16L 37/30 | 137/61 |
| 5,848,997 A ‡ | 12/1998 | Erskine | A61M 5/16831 | 604/53 |
| 5,957,151 A ‡ | 9/1999 | Dalcourt | B60C 23/001 | 137/22 |
| 6,045,542 A ‡ | 4/2000 | Cawood | A61F 5/4405 | 604/32 |
| 6,050,973 A ‡ | 4/2000 | Duffy | A61M 25/104 | 137/50 |
| 6,146,374 A ‡ | 11/2000 | Erskine | A61M 5/16831 | 604/53 |
| 6,298,873 B1 ‡ | 10/2001 | LeVey | F16K 15/142 | 137/102 |
| 6,655,656 B2 ‡ | 12/2003 | Maldavs | F16L 37/23 | 137/61 |
| 7,261,125 B1 ‡ | 8/2007 | Lien | F16L 37/098 | 137/61 |
| 7,727,188 B2 ‡ | 6/2010 | Machado | A61M 25/01 | 604/10 |
| 8,012,132 B2 ‡ | 9/2011 | Lum | A61M 5/348 | 604/24 |
| 8,016,816 B2 * | 9/2011 | Gregory | A61M 3/0283 | 604/540 |
| 8,052,671 B2 ‡ | 11/2011 | Christensen | A61B 5/412 | 604/54 |
| 8,814,899 B2 ‡ | 8/2014 | Pepper | A61M 25/0075 | 604/237 |
| 8,888,739 B2 ‡ | 11/2014 | Gregory | A61M 16/201 | 604/99 |
| 9,072,875 B2 ‡ | 7/2015 | Jin | A61F 5/4405 | |
| 9,623,201 B2 ‡ | 4/2017 | Gregory | A61M 16/208 | |
| 9,669,205 B2 ‡ | 6/2017 | Jin | F16L 37/38 | |
| 9,770,577 B2 * | 9/2017 | Li | A61M 29/02 | |
| 9,808,606 B2 ‡ | 11/2017 | Jin | A61M 25/1036 | |
| 9,993,250 B2 * | 6/2018 | Park | A61F 5/451 | |
| 2002/0134428 A1 ‡ | 9/2002 | Gabelmann | B60C 29/007 | 137/224 |
| 2003/0079752 A1 ‡ | 5/2003 | Hart | A61M 25/10187 | 128/88 |
| 2003/0106610 A1 ‡ | 6/2003 | Roos | B67D 3/043 | 141/34 |
| 2003/0221728 A1 * | 12/2003 | Enerson | F16K 15/026 | 137/541 |
| 2003/0229259 A1 ‡ | 12/2003 | Waksman | A61N 5/1002 | 600/3 |
| 2004/0010238 A1 ‡ | 1/2004 | Manera | A61J 7/0053 | 604/28 |
| 2004/0039374 A1 ‡ | 2/2004 | Tighe | A61M 39/20 | 604/53 |
| 2004/0158197 A1 ‡ | 8/2004 | Bellhouse | A61M 5/3015 | 604/70 |
| 2004/0176703 A1 ‡ | 9/2004 | Christensen | A61B 5/412 | 600/56 |
| 2005/0054996 A1 ‡ | 3/2005 | Gregory | A61M 3/0295 | 604/31 |
| 2005/0082828 A1 ‡ | 4/2005 | Wicks | F16L 37/38 | 285/31 |
| 2005/0101939 A1 ‡ | 5/2005 | Mitchell | A61M 39/1011 | 604/53 |
| 2005/0124932 A1 ‡ | 6/2005 | Foster | A61J 15/0065 | 604/99 |
| 2005/0256460 A1 ‡ | 11/2005 | Rome | A61M 39/26 | 604/24 |
| 2005/0273083 A1 ‡ | 12/2005 | Lebel | A61K 9/0024 | 604/89 |
| 2007/0123832 A1 ‡ | 5/2007 | Cline | A61F 5/445 | 604/33 |
| 2007/0142700 A1 ‡ | 6/2007 | Fogarty | A61F 5/41 | 600/40 |
| 2007/0149922 A1 ‡ | 6/2007 | Schneider | A61M 16/044 | 604/99 |
| 2007/0155224 A1 ‡ | 7/2007 | Marot | F16L 37/30 | 439/49 |
| 2007/0215221 A1 ‡ | 9/2007 | Lien | F16L 37/35 | 137/61 |
| 2008/0009794 A1 ‡ | 1/2008 | Bagaoisan | A61M 39/06 | 604/10 |
| 2008/0103463 A1 ‡ | 5/2008 | Tsai | B32B 7/12 | 604/31 |
| 2008/0114316 A1 ‡ | 5/2008 | Christensen | A61B 5/412 | 604/32 |
| 2008/0147012 A1 ‡ | 6/2008 | Rome | A61M 25/0097 | 604/16 |
| 2008/0175719 A1 ‡ | 7/2008 | Tracey | A61M 1/1086 | 417/38 |
| 2009/0029224 A1 ‡ | 1/2009 | Takahashi | F16L 37/34 | 429/44 |
| 2009/0163892 A1 ‡ | 6/2009 | McMichael | A61M 39/26 | 604/53 |
| 2010/0191192 A1 ‡ | 7/2010 | Prasad | A61M 39/24 | 604/24 |

(56) References Cited

U.S. PATENT DOCUMENTS

| | | | |
|---|---|---|---|
| 2010/0217189 A1‡ | 8/2010 | Pepper | A61M 25/10184 604/99 |
| 2010/0274189 A1‡ | 10/2010 | Kurth | A61M 25/1006 604/10 |
| 2010/0292640 A1‡ | 11/2010 | Kien | A61M 25/1018 604/99.02 |
| 2011/0152762 A1‡ | 6/2011 | Hershey | A61J 15/0015 604/99.02 |
| 2011/0196341 A1* | 8/2011 | Howell | A61M 25/10187 604/514 |
| 2011/0295236 A1* | 12/2011 | Gregory | A61M 1/85 604/540 |
| 2013/0030387 A1‡ | 1/2013 | Williams | A61M 39/26 604/25 |
| 2013/0071170 A1‡ | 3/2013 | Mehus | F16L 37/32 401/13 |
| 2013/0204125 A1* | 8/2013 | Chang | A61M 25/1006 600/425 |
| 2013/0237965 A1* | 9/2013 | Pinchuk | A61M 25/0017 604/544 |
| 2014/0052063 A1* | 2/2014 | Gregory | A61M 16/209 604/99.03 |
| 2014/0107572 A1‡ | 4/2014 | Jin | A61M 25/1036 604/99 |
| 2014/0276497 A1‡ | 9/2014 | Robinson | A61M 1/0056 604/32 |
| 2015/0051542 A1‡ | 2/2015 | Gregory | A61M 16/0443 604/97 |
| 2015/0059901 A1‡ | 3/2015 | Jin | F16L 37/32 137/79 |
| 2015/0080794 A1‡ | 3/2015 | Duong | A61M 1/10 604/97 |
| 2016/0325593 A1‡ | 11/2016 | Austin | B60C 29/002 |
| 2016/0339227 A1‡ | 11/2016 | Tsai | A61J 1/10 |
| 2017/0173310 A1‡ | 6/2017 | Gregory | A61F 5/445 |
| 2017/0252549 A1‡ | 9/2017 | Jin | A61M 39/26 |
| 2017/0259046 A9‡ | 9/2017 | Jin | A61M 39/24 |
| 2018/0229013 A1‡ | 8/2018 | Tsai | A61F 5/451 |

FOREIGN PATENT DOCUMENTS

| | | | |
|---|---|---|---|
| CN | 105407961 A | | 3/2016 |
| EP | 1514572 A2 | | 3/2005 |
| EP | 1514572 A2 | ‡ | 3/2005 |
| EP | 3027266 A1 | | 6/2016 |
| EP | 3027266 A1 | ‡ | 6/2016 |
| EP | 3297585 A1 | | 3/2018 |
| EP | 3297585 A1 | ‡ | 3/2018 |
| JP | S52158920 U | ‡ | 12/1977 |
| JP | S52158920 U | | 12/1977 |
| JP | S61192991 A | ‡ | 8/1986 |
| JP | S61192991 A | | 8/1986 |
| JP | H0629590 Y2 | | 8/1994 |
| JP | H0629590 Y2 | ‡ | 8/1994 |
| JP | H09327519 A | ‡ | 12/1997 |
| JP | H09327519 A | | 12/1997 |
| JP | H09512892 A | | 12/1997 |
| JP | H09512892 A | ‡ | 12/1997 |
| JP | 2003502588 A | | 1/2003 |
| JP | 2003502588 A | ‡ | 1/2003 |
| JP | 2007523296 A | ‡ | 8/2007 |
| JP | 2007523296 A | | 8/2007 |
| JP | 2008117545 A | ‡ | 5/2008 |
| JP | 2008117545 A | | 5/2008 |
| JP | 2011519629 A | ‡ | 7/2011 |
| JP | 2011519629 A | | 7/2011 |
| WO | 8300070 A1 | | 1/1983 |
| WO | 9530856 A1 | | 11/1995 |
| WO | WO-9530856 A1 | ‡ | 11/1995 |
| WO | 2004045704 A2 | | 6/2004 |
| WO | WO-2004045704 A2 | ‡ | 6/2004 |
| WO | 2006043883 A1 | | 4/2006 |
| WO | WO-2006/043883 | ‡ | 4/2006 |
| WO | 2009135141 A1 | | 11/2009 |
| WO | WO-2009135141 A1 | ‡ | 11/2009 ......... A61M 1/0084 |
| WO | 2011100187 A1 | | 8/2011 |
| WO | WO-2011100187 A1 | ‡ | 8/2011 |
| WO | 2013074763 A1 | | 5/2013 |
| WO | WO-2013074763 A1 | ‡ | 5/2013 |
| WO | 2013109293 A1 | | 7/2013 |
| WO | WO-2013109293 A1 | ‡ | 7/2013 |
| WO | 2015017646 A1 | | 2/2015 |
| WO | WO-2015017646 A1 | ‡ | 2/2015 |
| WO | 2016187350 A1 | | 11/2016 |
| WO | WO-2016187350 A1 | ‡ | 11/2016 |
| WO | 2017075226 A1 | | 5/2017 |
| WO | WO-2017075226 A1 | ‡ | 5/2017 |

OTHER PUBLICATIONS

New Zealand Patent Application No. 744299 Office Action dated Aug. 20, 2018.
U.S. Appl. No. 15/158,426 Office Action dated Aug. 27, 2018.
U.S. Appl. No. 15/448,274 Restriction Requirement dated Nov. 15, 2018.
U.S. Appl. No. 15/495,712 Advisory Action dated Dec. 13, 2018.
Japanese Patent Application No. 2016-531895 Office Action dated Jun. 11, 2019.
U.S. Appl. No. 15/158,426 Office Action dated Jun. 25, 2019.
U.S. Appl. No. 15/158,426 Office Action dated Mar. 4, 2019.
U.S. Appl. No. 15/448,274 Office Action dated Jul. 17, 2019.
U.S. Appl. No. 15/448,274 Office Action dated Mar. 5, 2019.
U.S. Appl. No. 15/495,712 Office Action dated Jan. 24, 2019.
Australian Patent Application No. 2017200016 Examination Report No. 1 dated Nov. 14, 2017.
Australian Patent Application No. 2017204860 Examination Report No. 1 dated May 29, 2018.
Australian Patent Application No. 2012340411 Examiner's First Report dated Jul. 14, 2016.
Australian Patent Application No. 2014296130 Office Action dated Apr. 13, 2018.
Chinese Patent Application No. 201280067212.0 Second Office Action dated Jul. 12, 2016.
Chinese Patent Application No. 201280067212.0 Third Office Action dated Feb. 27, 2017.
European Patent Application No. 12849279.0 Communication dated Aug. 18, 2016.
European Patent Application No. 12849279.0 Communication dated Mar. 23, 2016.
European Patent Application No. 14832568.1 Supplementary European Search Report dated Feb. 15, 2017.
Japanese Patent Application No. 2014-542455 Office Action dated Dec. 6, 2016.
Japanese Patent Application No. 2014-542455 Office Action dated Nov. 14, 2017.
Japanese Patent Application No. 2016-531895 Office Action dated Jul. 10, 2018.
Mexican Patent Application No. MX/a/2014/005934 Office Action dated Jul. 14, 2016.
New Zealand Patent Application No. 727366 First Examiner's Report dated Jan. 17, 2017.
PCT/US2012/025420 International Preliminary Report on Patentability dated Aug. 21, 2013.
PCT/US2012/025420 International Search Report and Written Opinion dated Jun. 6, 2012.
PCT/US2012/065239 International Preliminary Report on Patentability dated May 20, 2014.
PCT/US2012/065239 International Search Report dated Mar. 8, 2013.
PCT/US2012/065239 Written Opinion dated Mar. 8, 2013.
PCT/US2014/049115 International Preliminary Report on Patentability dated Feb. 11, 2016.
PCT/US2014/049115 International Search Report dated Oct. 28, 2014.
PCT/US2014/049115 Written Opinion dated Oct. 28, 2014.

(56) References Cited

OTHER PUBLICATIONS

PCT/US2016/033147 International Preliminary Report on Patentability dated Nov. 30, 2017.
PCT/US2016/033147 International Search Report and Written Opinion dated Aug. 16, 2016.
PCT/US2016/059132 International Preliminary Report on Patentability dated May 1, 2018.
PCT/US2016/059132 International Search Report and Written Opinion dated Jan. 6, 2017.
Russian Patent Application No. 2014124144 Office Action dated Nov. 14, 2016.
Russian Patent Application No. 2016107147 Office Action dated Apr. 24, 2018.
Taiwanese Patent Application No. 101142959 Office Action dated Mar. 21, 2016.
Taiwanese Patent Application No. 105113600 Office Action dated Jan. 16, 2017.
U.S. Appl. No. 13/877,890 Office Action dated Mar. 27, 2014.
U.S. Appl. No. 14/000,384 Office Action dated Sep. 11, 2014.
U.S. Appl. No. 14/341,647 Office Action dated May 5, 2016.
U.S. Appl. No. 14/449,035 Office Action dated Feb. 12, 2016.
U.S. Appl. No. 14/449,035 Office Action dated Sep. 14, 2016.
U.S. Appl. No. 14/745,312 Office Action dated Feb. 17, 2016.
U.S. Appl. No. 15/495,712 Office Action dated Jan. 5, 2018.
U.S. Appl. No. 15/495,712 Office Action dated Sep. 5, 2018.
U.S. Appl. No. 15/495,712 Restriction Requirement dated Oct. 6, 2017.
Canadian Patent Application No. 2,855,366 Office Action dated Aug. 29, 2018.
Chinese Patent Application No. 201480043509.2 Office Action dated Aug. 30, 2018.
EP16797245.4 Extended European Search Report dated Nov. 12, 2018.
New Zealand Patent Application No. 727366 Office Action dated Aug. 20, 2018.
Chinese Office Action; The State Intellectual Property Office of the People's Republic of China; Chinese Application No. 201680077290.7; dated Dec. 15, 2020; 16 pages.

\* cited by examiner
‡ imported from a related application

VALVE SYSTEM FOR INFLATABLE DEVICES

This application is a divisional of U.S. application Ser. No. 15/772,020, filed on Apr. 27, 2018, which is a U.S. National Phase of International Application No. PCT/US2016/059132, filed on Oct. 27, 2016, which claims the benefit of U.S. Provisional Application No. 62/247,934, filed on Oct. 29, 2015, each of which is incorporated herein by reference in its entirety.

CROSS-REFERENCE

This application claims the benefit of U.S. Provisional Application No. 62/247,934 filed Oct. 29, 2015, which application is incorporated herein by reference.

BACKGROUND OF THE INVENTION

Indwelling medical devices are a common and indispensable part of medical care. Indwelling devices may be placed within a bodily organ or passage to promote drainage of fluid matter from the body, for example, via a catheter. Indwelling medical devices may have an inflatable portion such as a retention balloon for retaining and/or sealing the catheter within the body. Proper inflation is used for retaining the catheter within the body and deflated for insertion into and removal from the body, without harming the patient.

Indwelling medical devices are used in fecal management systems (FMS) to enable the temporary diversion and containment of waste fluids in patients who are often bedridden, immobilized, and/or fecal incontinent. FMS can protect wounds from fecal contamination, reduce the risk of skin breakdown, reduce the spread of infection, and provide a safe and effective alternative to traditional methods of fecal incontinence such as pads, diapers, and fecal pouches.

SUMMARY OF THE INVENTION

Fecal incontinence is a common condition affecting patients in intensive care units and places a heavy burden on hospital personnel and carries significant risks to patients. Complicated and harmful effects include skin breakdown and the development of pressure ulcers, as well as the spread of C. difficile, an infectious bacterium that can be found in diarrhea.

In fecal management systems, a retention balloon is located at the distal end of a catheter. The retention balloon may be inserted into the body in a deflated condition and positioned inside the rectal cavity. Once properly positioned, the retention balloon may be inflated via an inflation port which may be located on a distal end of a tube that provides a passageway to the retention balloon and extends along the catheter on the outside of the body. It is important that the retention balloon is not over-inflated and does not exceed pre-determined pressures. The present disclosure provides valves and valve systems for the prevention of over-inflation of inflatable indwelling medical devices, including fecal management systems. Additional indwelling medical devices include catheter balloon dilatations which am widely used to dilate areas of narrowing in blood vessels, ureters, and in the gastrointestinal tract, such as urinary catheters, airway catheters, tracheal catheters, drainage devices, patency devices, devices for the administration of therapeutics and drugs, feeding tubes, and the like.

In one aspect, provided herein is an apparatus for limiting fluid pressure within an inflatable portion of an inflatable device, wherein the inflatable device comprises a supply fluid path and a return fluid path individually connecting the inflatable portion to the apparatus, the apparatus comprising: a body comprising a fluid inlet port and a fluid outlet port connected by a first passage, wherein the first passage is connected to the supply fluid path at the fluid outlet port; a second passage connected to the return fluid path, wherein the first passage and the second passage are not in fluid communication within the apparatus; and wherein a pressure relief valve is located such that when the fluid pressure in the inflatable portion and the second passage exceeds a predetermined pressure, the pressure relief valve opens and excess fluid is released from the inflatable portion. In some embodiments, the first passage of the apparatus is not obstructed when the pressure within the inflatable portion exceeds the predetermined pressure, such that the apparatus is configured to allow for the inflatable portion to receive fluid via the first passage when the pressure within the inflatable portion exceeds the predetermined pressure. In some embodiments, the predetermined pressure is the cracking pressure of the pressure relief valve. In some embodiments, the predetermined pressure is from about 30 mm Hg to about 90 mm Hg, or born about 50 mm Hg to about 70 mm Hg. In some embodiments, the pressure relief valve comprises an umbrella valve, spring loaded ball valve, spring loaded poppet valve, rupturing disk, or a combination thereof. In some embodiments, the pressure relief valve has a height no greater than about 20, 15, 10, 9, 8, 7, 6 or 5 mm. In some embodiments, the pressure relief valve is positioned within the second passage. In some embodiments, the apparatus further comprises a fill indicator located at the second passage of the apparatus. In some embodiments, the pressure relief valve is not ferromagnetic. In some embodiments, the fill indicator is a pressure indicator comprising a mechanical element configured to alternate between a first physical state and a second physical state when a pressure within the inflatable portion meets or exceeds an optimal fill pressure. In some embodiments, the optimal fill pressure is from about 10 mm Hg to about 60 mm Hg. Further provided herein is the inflatable medical device. In some embodiments, the inflatable portion of the inflatable medical device has a maximum fill volume, at which point the pressure within the inflatable portion is the predetermined pressure. In some embodiments, the maximum fill volume is from about 35 ml to about 50 ml. In some embodiments, the maximum fill volume is about 50 ml±5 ml.

In another aspect, provided herein is an inflatable indwelling medical device comprising: (a) an apparatus comprising a fluid inlet port and a fluid outlet port connected by a first passage, and a second passage; wherein the first passage and the second passage are not connected within the apparatus; and (b) a retention balloon; wherein a supply fluid path connects the first passage of the apparatus at the fluid outlet port to the retention balloon, and a return fluid path connects the second passage of the apparatus to the retention balloon, wherein the second passage comprises a pressure relief valve that opens to relieve pressure within the retention balloon when the pressure within the retention balloon reaches a predetermined pressure. In some embodiments, the predetermined pressure is from about 30 mm Hg to about 90 mm Hg, or from about 50 mm Hg to about 70 mm Hg. In some embodiments, the apparatus further comprises a fill indicator that provides notification when the retention balloon is filled to or above an optimal fill pressure, the fill indicator positioned within the second passage. In some embodiments, the optimal fill pressure is from about 30 mm Hg to about 60 mm Hg. In some embodiments, the pressure relief valve comprises an umbrella valve, spring loaded ball valve, spring loaded poppet valve, rupturing disk, or a combination thereof. In some embodiments, the retention balloon is positioned at the distal end of a catheter for insertion into a body cavity of a patient, and the proximal end of the catheter is configured for coupling to a collection bag.

In another aspect, provided herein is a method of filling an inflatable portion of a device to a predetermined operating range, the method comprising: (a) providing the device comprising the inflatable portion, the inflatable portion being in fluid communication with (i) an inflation port via a first passage, and (ii) a fill indicator and a pressure relief valve in a closed configuration, via a second passage; wherein the inflatable portion has a minimum operating fill volume and a maximum operating fill volume, and a fill volume between and including the minimum and maximum operating fill volumes is the predetermined operating range of the inflatable portion, and wherein the first passage and the second passage are enclosed within an apparatus, and the first passage and the second passage are not in fluid communication within the apparatus, (b) providing a fluid to the inflatable portion through the inflation port and the first passage to fill the inflatable portion until the fill indicator indicates that the minimum operating fill volume is achieved; and (c) optionally continuing to provide the fluid to the inflation portion through the inflation port and the first fluid passage until: (i) the pressure relief valve opens into an open configuration to restrict the inflation portion from being filled beyond the maximum operating fill volume, or ii) before the pressure relief valve opens into the open configuration. In some embodiments, the pressure relief valve opens at a cracking pressure from about 30 mm Hg to about 90 mm Hg, or from about 50 mm Hg to about 70 mm Hg. In some embodiments, the inflatable portion is inserted into a cavity of a subject. In some embodiments, the predetermined operating range of the inflatable portion is determined by the identity and/or dimensions of the cavity of the subject. In some embodiments, the method comprises selecting a cracking pressure of the pressure relief valve depending on the cavity of the subject. In some embodiments, the minimum operating fill volume is from about 30 ml to about 45 ml, or from about 35 ml to about 45 ml. In some embodiments, the maximum operating fill volume is from about 45 ml to about 70 ml, or from about 45 ml to about 55 ml. In some embodiments, the pressure relief valve is positioned on a valve seat, and wherein a cracking pressure of the pressure relief valve is dependent on the height of the valve seat. In some embodiments, the pressure relief valve comprises an umbrella valve, spring loaded ball valve, spring loaded poppet valve, rupturing disk, or a combination thereof. In some embodiments, the pressure relief valve has a height no greater than about 20, 15, 10, 9, 8, 7, 6 or 5 mm. In some embodiments, the fill indicator is a pressure indicator comprising a mechanical element configured to alternate between a first physical stale and a second physical state when a pressure within the inflatable portion meets or exceeds minimum operating fill volume.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

In fecal management systems, a distally placed retention balloon may be inserted into the body in a deflated condition and positioned inside the rectal cavity. It is important that the retention balloon is not over-inflated and does not exceed pre-determined pressures in the patient. Complications of over-inflation include bruising, ulceration, tissue necrosis and infection in the patient. Challenges for controlling and maintaining proper and adequate pressure in the retention balloon include a limited footprint in the medical devices to incorporate pressure relief and maintenance systems, including safety concerns for patients, adequate pressure control and prevention of pressure spikes if incorporated into the inlet or inflation lumen of the retention balloon, and the low pressure maintained in the retention balloon, presenting a technical challenge in maintaining pressures in the range of 10 mm Hg to 100 mm Hg (approximately 0.2 psi to 2 psi).

The present invention provides valves and valve systems, including pressure relief valves, for the prevention of over-inflation of inflatable indwelling medical devices, including fecal management systems. In some embodiments, the pressure relief valve is incorporated into the outlet or returning lumen of the retention balloon system in order to address the challenges presented in low pressure maintenance and control. In addition, the pressure relief valves described herein may be mechanical, with a small footprint or dimension, allowing operation within the low pressure maintenance systems used in these indwelling medical devices. Additional indwelling medical devices include catheter balloon dilatations which are widely used to dilate areas of narrowing in blood vessels, ureters, and in the gastrointestinal tract, such as urinary catheters, airway catheters, tracheal catheters, drainage devices, patency devices, devices for the administration of therapeutics and drugs, feeding tubes, and the like.

Figure 1:
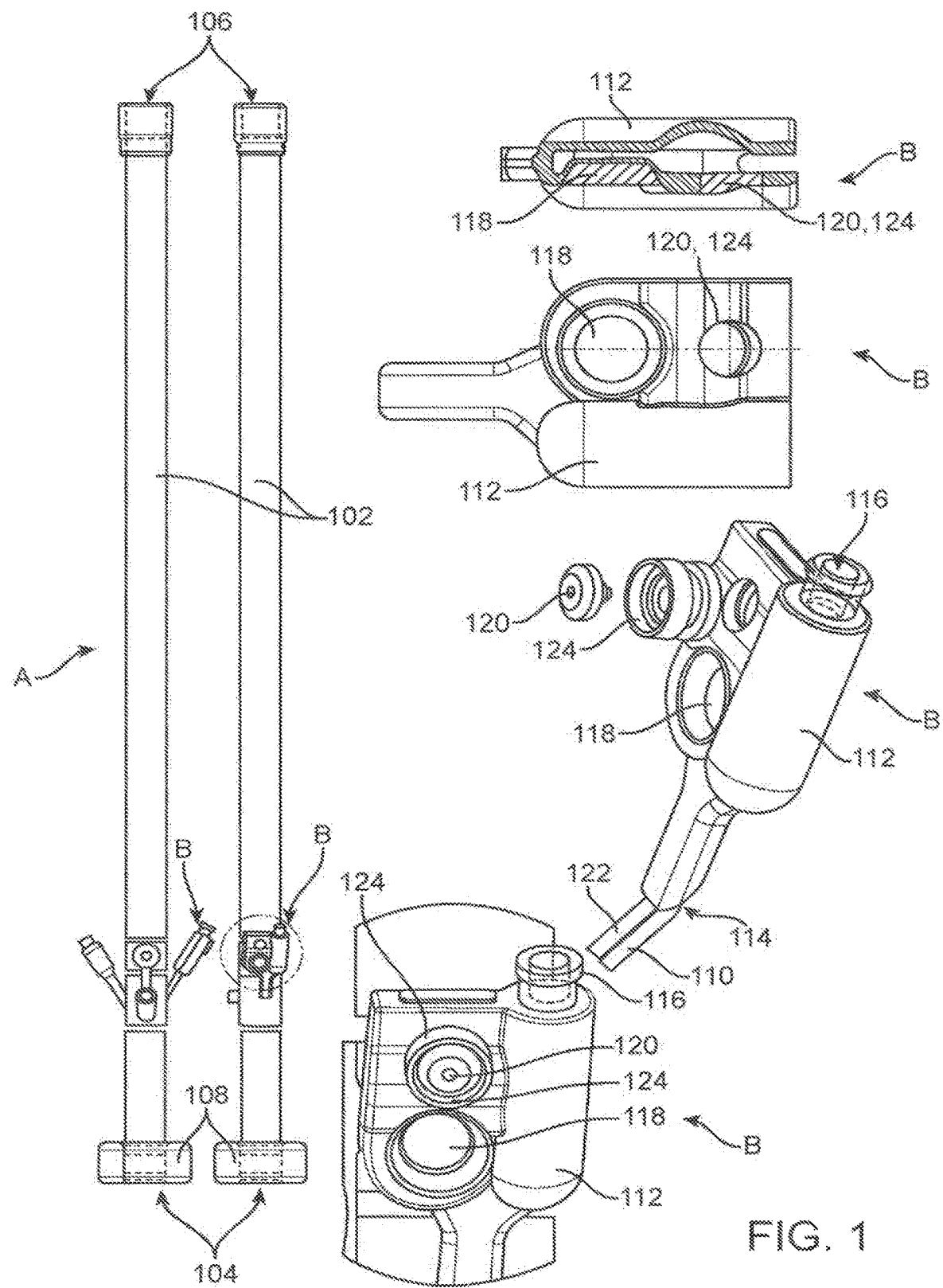
FIG. 1 is an embodiment of an inflatable indwelling medical device comprising a retention balloon and a valve system B for preventing over-inflation of the retention balloon.

Referring to FIG. 1, an embodiment of an inflatable indwelling medical device A is shown comprising a valve system B and an elongated flexible tubular element 102 having a distal end 104 for positioning the device A into a body cavity of a patient. The proximal end 106 of tubular element 102 may connect to a receptacle to collect waste from the patient that drains through an interior of the tubular element 102 when the device A is positioned within the patient. Affixed to the exterior surface of the distal end 104 of the tubular element 102 is an inflatable retention balloon 108, shown in its inflated state, that serves to anchor the distal end 104 of the device A in the body cavity.

Retention balloon 108 is connected to a valve system B through a supply fluid path provided by a supply lumen 110 and return fluid path provided by a return lumen 122. Valve system B is designed for limiting fluid pressure within the retention balloon 108 during inflation and when the retention balloon 108 is held within the body cavity. The body 112 of valve system B comprises an inlet port 116 for receiving a connector associated with a source of fluid for inflation of the retention balloon 108, and an outlet port 114 connected to the supply fluid path, the inlet port 116 and outlet port 114 connected via a first passage within body 112.

Valve system B further comprises a second passage connected to the return fluid path, the second passage composing a fill indicator 118 and pressure relief valve 120. The second passage is connected to the retention balloon 108 via the return fluid path such that the second passage receives the pressure from retention balloon 108. If the pressure within the retention balloon 108 exceeds a first pressure, for example, during inflation, the fill indicator 118 provides a notification, such as a visual and/or audible notification, to the practitioner filling the retention balloon 108 to remove excess fluid from the retention balloon 108 via the inflation port 116. If the pressure within the retention balloon 108 exceeds a second pressure, the pressure relief valve 120 will open, releasing excess fluid from the retention balloon 108 through the second passage of the valve system. The second pressure may be the same or greater than the first pressure. In some cases, the first pressure is an optimal pressure of the retention balloon 108, so that the fill indicator 118 notifies a practitioner filling the retention balloon 108 that the optimal pressure has been met and to halt inflation. If the fill indicator 118 is a mechanical element, a first state of the fill indicator 118 may indicate under-inflation whereas the second state may indicate both optimal inflation and over-inflation.

In this figure, the pressure relief valve 120 and the fill indicator 118 are situated in the second passage and the inflation port 116 is within the first passage to the retention balloon 108. In this exemplary configuration, there is not an interaction between the second passage from the first passage other than the housing of the valve system body 112, thus minimizing the footprint of user interaction with these components.

The fill indicator 118 shown in FIG. 1 comprises a dome positioned over the second fluid passage. When the first pressure is reached, the dome expands outward to provide a visual indication that the first pressure has been reached. However, fill indicator 118 may alternatively or additionally provide a pneumatic or electronic indication of when the first pressure is reached, for example, via a solenoid valve, pneumatic valve, light emitting diode (LED) or other light, audible sound, wireless beeping, or the like.

The pressure relief valve 120 shown in FIG. 1 is an umbrella valve situated on a valve seat 124. However, other pressure relief valves useful for a valve system provided herein are envisioned. As a non-limiting example, a valve system may comprise a spring loaded ball valve, a spring loaded poppet valve, a rupturing disc, or a combination thereof. Generally the pressure relief valve is selected to have a cracking pressure (i.e. minimum pressure required to open the valve) within the valve system that corresponds to a maximum pressure of the retention balloon 108 to which it is connected.

The valve system B shown in FIG. 1 is useful for limiting the pressure of retention balloon 108 during inflation or when device A is maintained within the body cavity of the patient. Methods of using valve system B for this purpose include: (a) providing an inflatable indwelling medical device A as generally shown in FIG. 1, (b) inserting the retention balloon 108 into the body cavity, and (c) introducing fluid into the retention balloon 108 via a source of fluid connected to inflation port 116 of valve system B; wherein if a first pressure of the retention balloon 108 is achieved, fill indicator 118 will provide an indication of such pressure and excess fluid may with withdrawn through inflation port 116 until the pressure within the retention balloon 108 is reduced below the first pressure; and wherein if a second pressure of the retention balloon is achieved, the pressure relief valve 120 opens, releasing excess fluid from the retention balloon 108. For cases where the pressure relief valve can return to a non-open state (e.g., umbrella valve, spring loaded ball valve, spring loaded poppet valve), when the pressure within retention balloon 108 is reduced below the second pressure, the pressure relief valve returns to the non-open state.

In some embodiments, the inflation port 116 comprises a Luer fitting that connects to a Luer lock syringe that serves as a source of fluid. In some cases, engagement of the source of inflation fluid to the inflation port 116 allows access of fluid to a Leur check valve, and when a certain pressure is met, allows for the opening of the Leur check valve. In some cases, engagement of the source of inflation fluid to the inflation port 116 opens a seal, allowing for access to a Leur check valve. The Luer check valve may comprise a body, stem and plug. In some cases, the stem comprises an elastic rubber. The Luer check valve may be normally closed such that when the stem of the valve is compressed by the Luer tip of the source of inflation fluid (i.e., syringe), it opens up a fluid path to allow for passage of the fluid into the first passage of the valve system B.

Figure 2A:
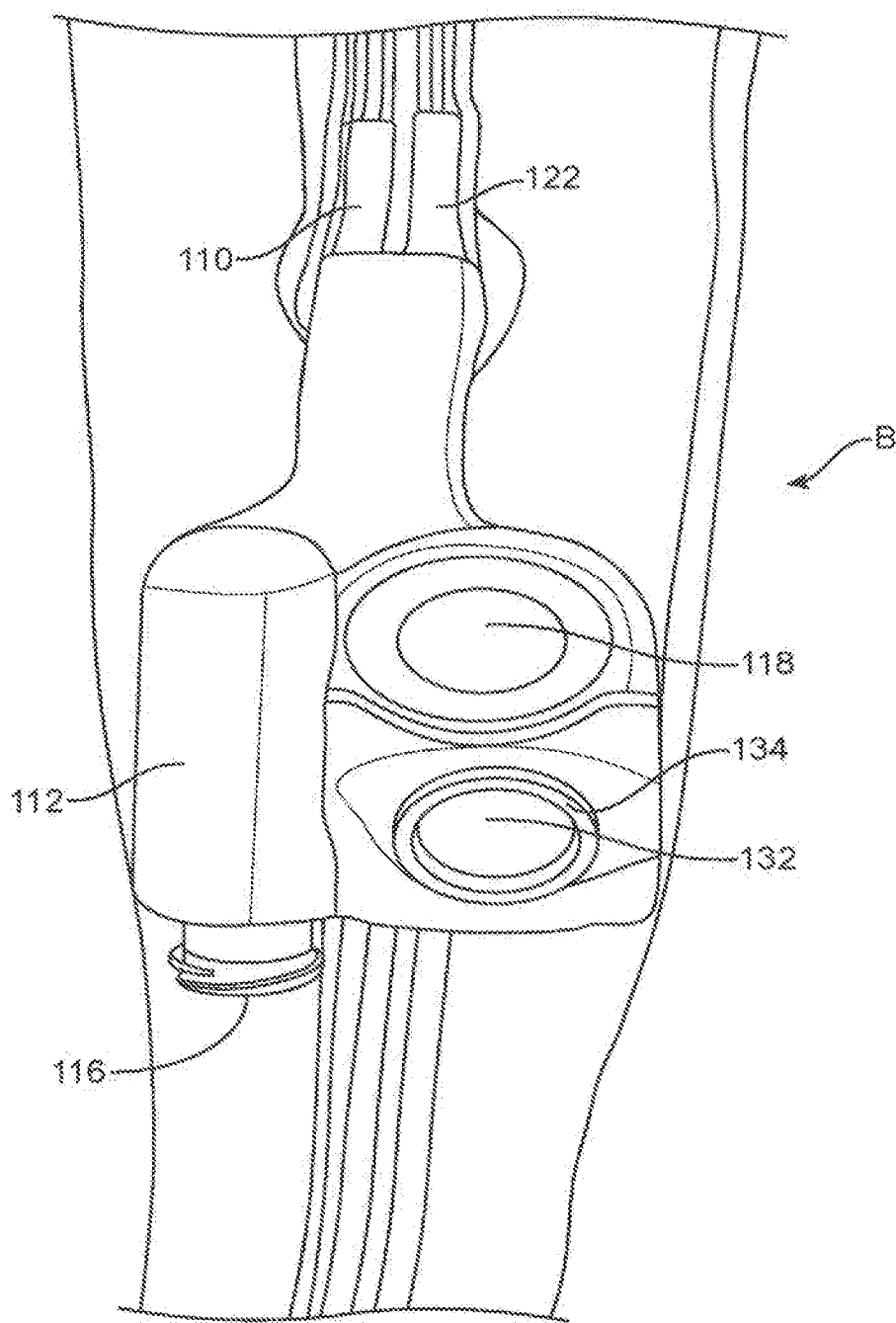
FIG. 2A is an embodiment of a valve system B comprising an umbrella valve.
Figure 2B:
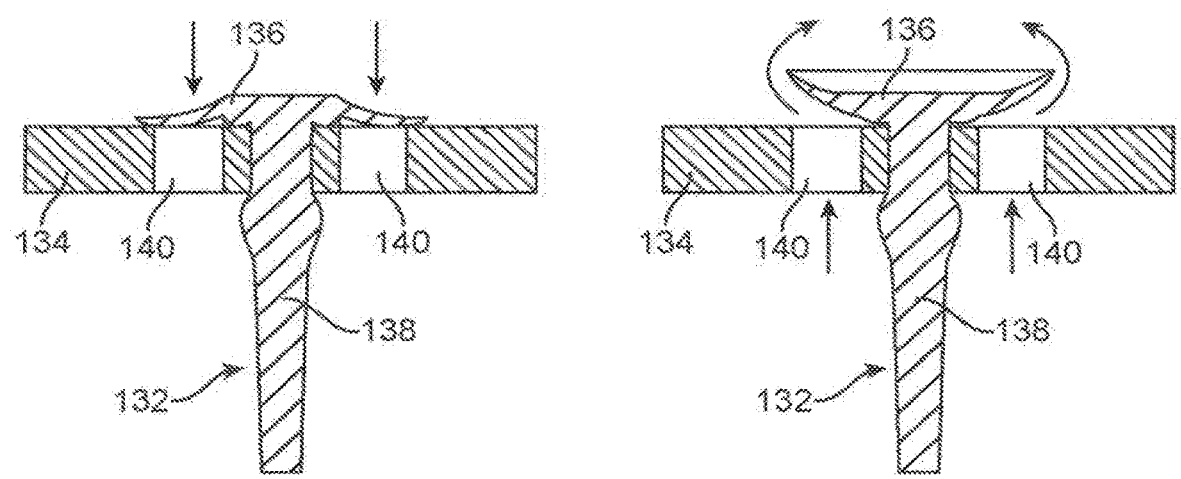
FIG. 2B is an embodiment of an umbrella valve for use in a valve system provided herein.

An embodiment of a valve system B comprising an umbrella valve 132 as a pressure relief valve is shown in FIG. 2A. As described in FIG. 1, valve system B comprises first and second passages enclosed within a body 112. For the valve system B shown in FIG. 2A, situated within the second passage is a fill indicator 118 and an umbrella valve 132 seated on a valve seat 134. A detailed view of umbrella valve 132 and valve seat 134 is shown in FIG. 2B. Umbrella valve 132 comprises a sealing disk 136 which flattens against the valve seat 134 with a certain sealing force, and a stem 138. The sealing disk 136 may have elastic material properties and convex shape to create the sealing force, while the stem 138 is used to hold the umbrella valve 132 in place so as to avoid the need for additional components such as a spring or positioner. The valve seat 134 comprises vents 140. When a force exerted on the sealing disk 136 through vents 140 is sufficient to lift the convex diaphragm from the seat 134, the umbrella valve 132 allows for flow to occur in a forward direction (FIG. 2B, right panel), while preventing back flow in the opposite direction (FIG. 2B, left panel). The umbrella valve 132 is orientated such that the forward direction is the direction that fluid takes as it leaves the body 112 from the second passage, through umbrella valve 132. Umbrella valve 132 may be selected such that the force necessary to open the umbrella valve 132 corresponds to a predetermined pressure of retention balloon 108 that is conferred to the second passage of the valve system B. The predetermined pressure may correspond to the cracking pressure of the umbrella valve 132, which may be from about 30 mm Hg to about 90 mm Hg, or from about 50 mm Hg to about 70 mm Hg.

Figure 3A:
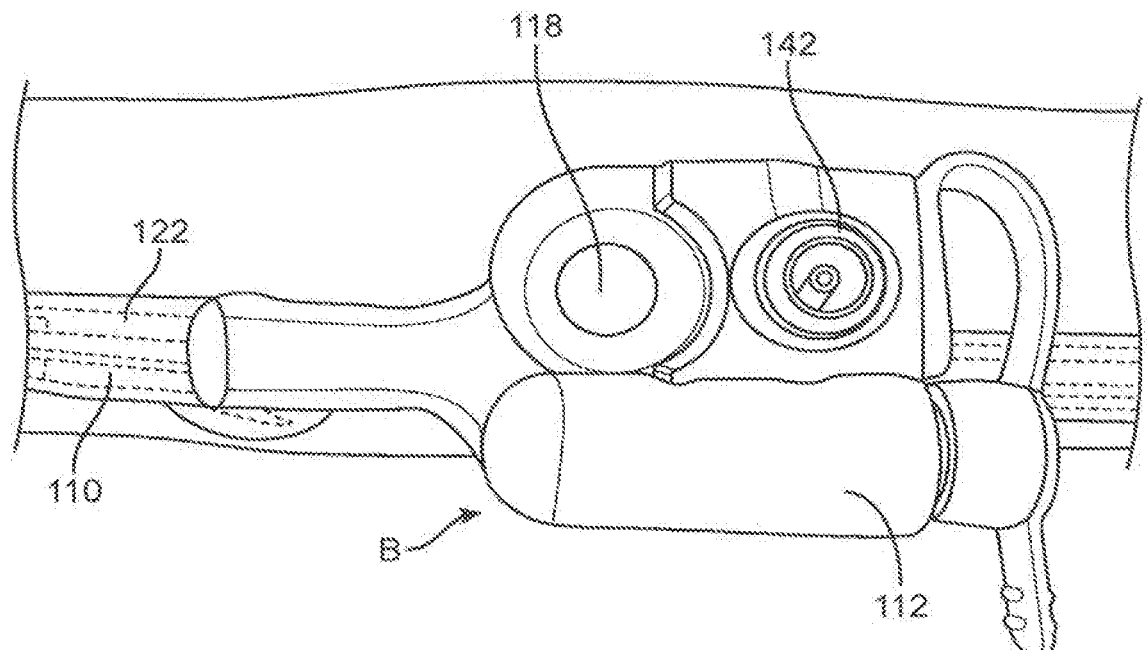
FIG. 3A is an embodiment of a valve system B comprising a spring loaded ball valve.
Figure 3B:
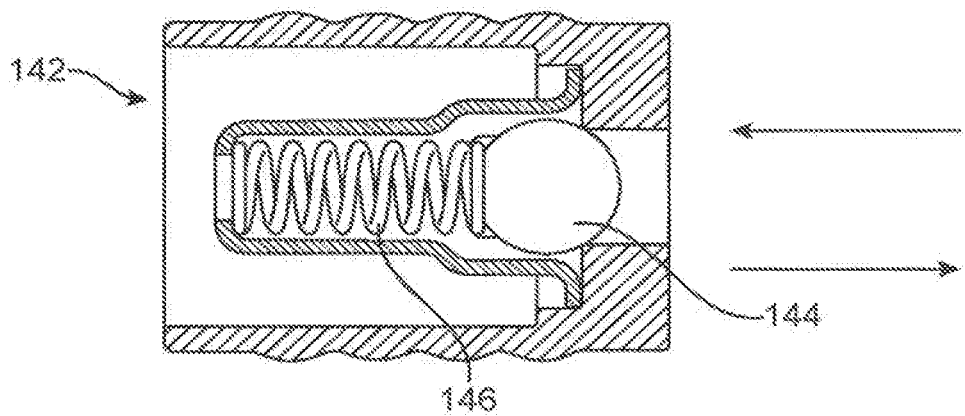
FIG. 3B is an embodiment of a spring loaded ball valve for use in a valve system provided herein.

An embodiment of a valve system B is shown in FIG. 3A, comprising a spring loaded ball valve 142 that releases fluid when a predetermined pressure is exceeded, and then closes when the pressure drops below the predetermined level. A detailed view of the spring loaded ball valve is shown in FIG. 3B. The spring loaded ball valve 142 comprises a ball 144 positioned against a spring 146, such that when the pressure of fluid within the balloon 108 exceeds a predetermined level, the fluid exerts a force on the ball 144 that compresses spring 146 to allow the fluid to move in a forward direction. A spring loaded ball valve 142 may be selected such that the force necessary to compress ball 144 corresponds to a predetermined pressure of balloon 108 that is recognized at the valve system B. The predetermined pressure may correspond to the cracking pressure of the spring loaded ball valve 142, which may be from about 30 mm Hg to about 90 mm Hg, or from about 50 mm Hg to about 70 mm Hg. In some embodiments, the cracking pressure is about 60 mm Hg.

Figure 4A:
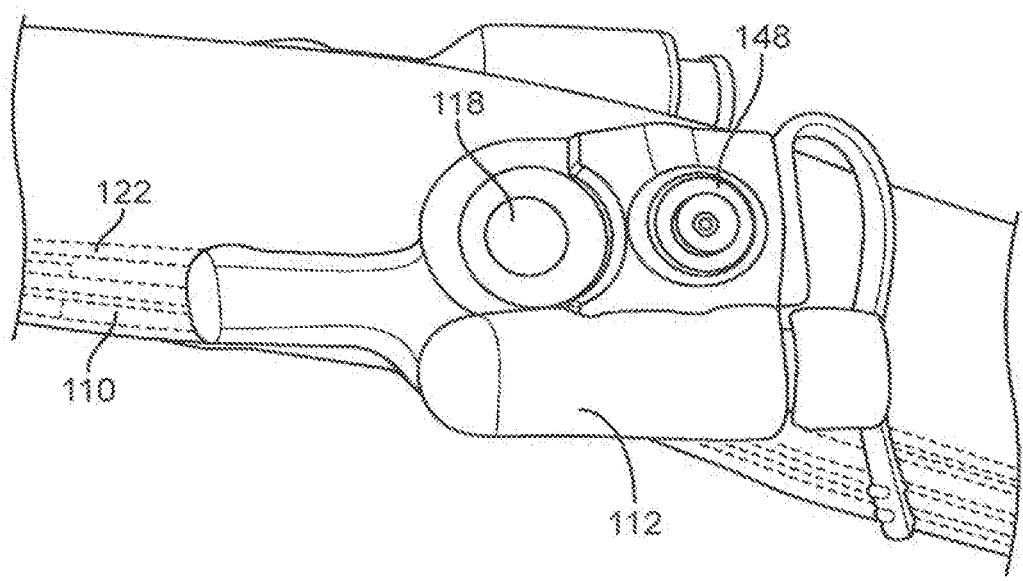
FIG. 4A is an embodiment of a valve system B comprising a spring loaded poppet valve.

An embodiment of a valve system B comprising a spring loaded poppet valve 148 is shown in FIG. 4A. The spring loaded poppet valve 148 (FIG. 4B) is positioned within the valve system B such that the spring of the poppet valve 148 and the pressure from within the second passage apply opposing forces on the spring loaded poppet valve 148. When the force from the second passage exerts a greater force than the spring force (i.e. the cracking pressure), then the poppet moves away from a valve seat, allowing thud to pass through an outlet port of the spring loaded poppet valve 148. As the pressure within the second passage drops below the cracking pressure of the valve, the valve closes.

Figure 5:
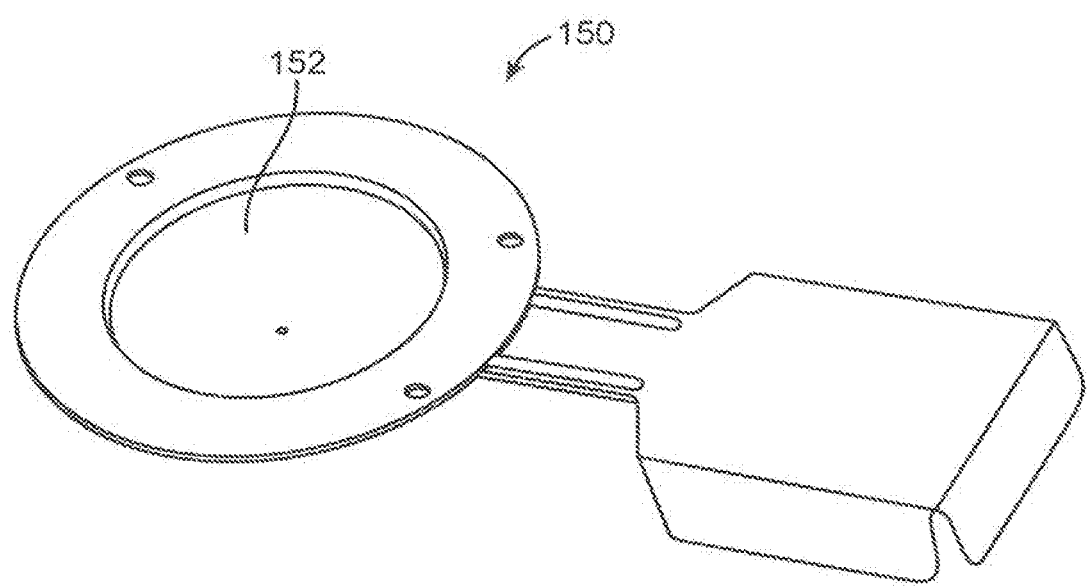
FIG. 5 is an embodiment of a rupturing disc for use in a valve system provided herein.

Another type of pressure relief valve useful in a valve system B provided herein is a rupturing disc 150, as shown in FIG. 5. The rupturing disc comprises a one-time-use membrane 152 that ruptures at a predetermined differential pressure. In some cases, a valve system provided herein comprises a first pressure relief valve and as a backup device, a rupturing disc. For instance, if the pressure increases and the first pressure relief valve fails to operate or does not relieve enough pressure fast enough, the rupturing disc will burst.

Valve Systems

Figure 10:
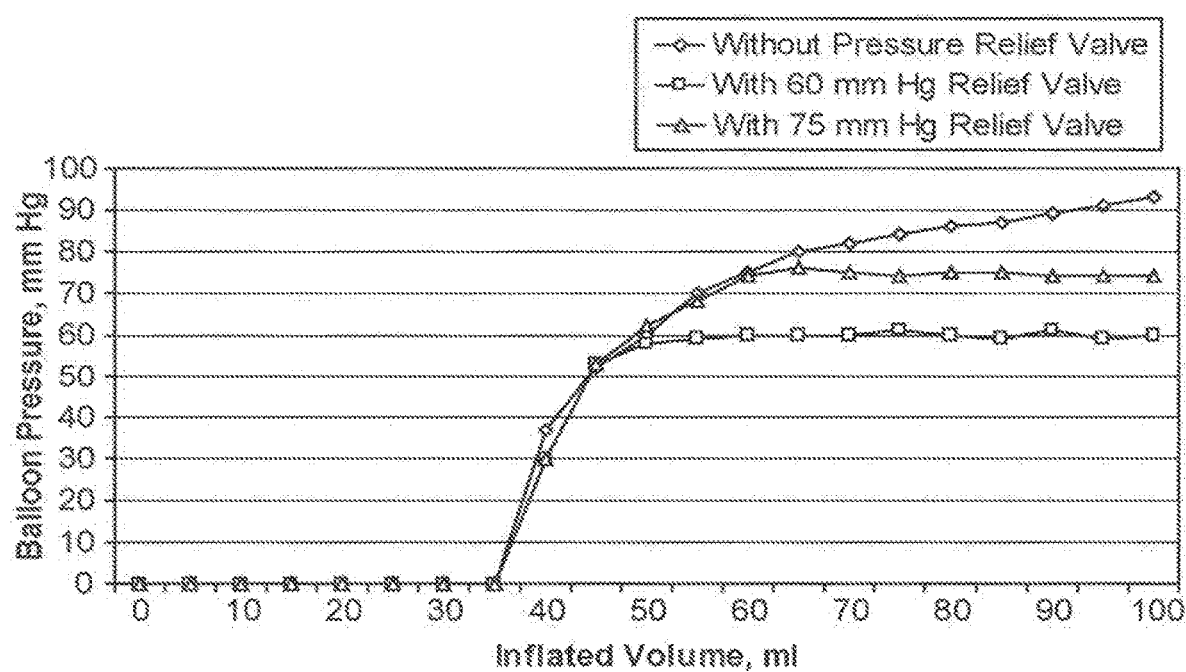
FIG. 10 is a plot of balloon pressure versus the inflated volume of the balloon when the balloon is inflated with water in systems having or not having a pressure relief valve. One system comprised a pressure relief valve having a 60 mm Hg cracking pressure, and another system comprised a pressure relief valve having a 75 mm Hg cracking pressure.

In one aspect of the disclosure, valve systems provided herein have a first and a second passage that are non-interfering or non-interacting. This is distinctively different from previously described valve systems, such as those described in US 2015/0051542. For example, when the pressure of the present valve systems exceeds the pre-determined fill pressure, the first passage can continue to be filled in the present disclosure if the cracking pressure is set as such. Thus, the systems herein allow for the cracking pressure to be set above the pre-determined filled pressure, while the valve system described in US 2015/0051542 would stop the flow from the first passage as soon as the pressure in the second passage reaches the pre-determined filled pressure. Such a design in the present disclosure has an advantage in a clinical use not achievable through the valve system in US 2015/0051542. Since the optimum fill pressure varies from patient to patient, valve systems with restricted flexibility of the operating window allow the fill pressure to be varied due to patients. For example, the rectal pressure in an obese patient may be higher than the rectal pressure of a patent with an average weight and rectum size. As a result, the fill pressure in an obese patient population may need to be adjusted above the optimum fill pressure in order to allow the balloon to be inflated and thus anchored inside the rectum. With a proper choice of the cracking pressure to be set above the optimum fill pressure, the present described systems allow for the balloon to be filled at a pressure range above the optimum fill pressure. The optional fill indicator in the device offers a cue or signal to the proper fill volume. At the same time, the cracking pressure of the pressure relief valve prevents the significant over-inflation that is harmful to the patient. This is illustrated in FIG. 10, where there is a range of from 40 ml to 50 ml filled volume to allow for balloon inflation when a 60-mm-Hg pressure relief valve is used in one embodiment of the present invention. FIG. 10 also shows dial in this embodiment, there is a range of from 40 ml to 60 ml filled volume to allow for balloon inflation when a 75-mm-Hg pressure relief valve is used. Such a wider operating range of the present systems allows a clinician to inflate rectal balloon in most patients without the restrictions necessary using the systems of US 2015/0051542, where the operating range of the filled volume on a specific patient was very narrow. The use of the optional fill indicator adds another safety feature to allow clinician to judge the onset of optimum filled volume (thus balloon pressure).

Pressure Relief Valves

Provided herein are valve systems comprising a pressure relief valve having an open configuration and a closed configuration to permit or deny, respectively, the passage of fluid to and/or from an inflatable portion of an inflatable indwelling medical device. As discussed, a pressure relief valve is located within a second passage of the valve system so that any pressure spikes that may occur during inflation via the first passage do not prematurely open the valve.

The pressure relief valve is selected in part to have a limited footprint in the valve system of an inflatable indwelling medical device. A small footprint minimizes the chance of developing a pressure sore when a patient lies over the valve system or rubs against it such as may be the case with a fecal catheter. Foley catheter and air way catheter, which are intimately close to sensitive areas of the body. In some embodiments, the height of a valve system comprising a pressure relief valve is less than or about 50 mm, 40 mm, 30 mm, 20 mm, 15 mm or 10 mm. In some embodiments, the height of a pressure relief valve is less than or about 50 mm, 40 mm, 30 mm, 20 mm, 15 mm or 10 mm. In some cases, the height of a valve system is less than about 20 mm. In some cases, the height of a pressure relief valve is less than about 20 mm. In some cases, the height of a pressure relief valve is less than about 15 mm. In some cases, the height of a pressure relief valve is less than about 10 mm.

The pressure relief valve is also selected for the cracking pressure, or the minimum pressure within the second passage to force the valve open. The pressure relief valve may be selected so that its cracking pressure corresponds to the pressure limitations required for the particular inflatable indwelling medical device. In some instances, the cracking pressure is met during inflation of the inflatable portion of the device. In some instances, the cracking pressure is met after balloon inflation, for example, the cracking pressure is achieved by pressure changes within the inflatable portion which may be caused by pressure changes within a patient's body, including pressure changes caused by coughing, sneezing, peristalsis, movement, sitting, and crying.

In some embodiments, a c nicking pressure of a valve in a system described herein is from about 10 mm Hg to about 120 mm Hg, about 10 mm Hg to about 100 mm Hg, about 10 mm Hg to about 90 mm Hg, about 10 mm Hg to about 80 mm Hg, about 10 mm Hg to about 70 mm Hg, about 20 mm Hg to about 90 mm Hg, about 20 mm Hg to about 80 mm Hg, about 30 mm Hg to about 90 mm Hg, about 30 mm Hg to about 80 mm Hg, about 40 mm Hg to about 90 mm Hg, about 40 mm Hg to about 80 mm Hg, about 50 mm Hg to about 80 mm Hg, or about 50 mm Hg to about 70 mm Hg. The cracking pressure may be from about 50 mm Hg to about 70 mm Hg. In some cases, the cracking pressure of a valve is about within a system described herein is about 30 mm Hg to about 90 mm Hg. The tolerance may be about ±5%, 6%, 7%, 8%, 9%, 10%, 11%, 12%, 13%, 14%, 15%, 16%, 17%, 18%, 19% or 20%. In some cases, the tolerance is about a ±15%. The cracking pressure may be from about 50 mm Hg to about 70 mm Hg with a tolerance of about ±15%. In some cases, the cracking pressure of a valve is about 30, 35, 40, 45, 50, 55, 60, 65, 70, 75, 80, 85 or 90 mm Hg with a tolerance of ±10 mm Hg or preferably ±5 mm Hg. In various embodiments, a rate of fluid flow within a lumen of a valve system is dependent on the cracking pressure of a valve of the system.

Pressure relief valves useful in the systems provided herein include blow-off valves or cracking pressure check valves, wherein the valves open when a set pressure is reached. For example, once a predetermined pressure is reached within a valve system, the valve opens to release the pressure, preventing over-inflation of an inflatable portion of an inflatable indwelling medical device. Non-limiting examples of pressure relief valves useful in the valve systems described herein include umbrella valves, duckbill valves, split valves, metal spring valves, film valves, and Belleville valves. In some embodiments, the valve is flanged. In other embodiments, the valve is sleeved. In some embodiments, the valve is a combination valve, for example, a valve comprising two or more valves in one single component. In some cases, a combination valve comprises a duckbill and an umbrella.

The pressure relief valve may be a one-way valve that creates unidirectional flow in a device. In such instances, the pressure relief valve may comprise elastomeric sealing elements that allow forward flow and prevent backflow. Non-limiting examples of one-way valves include an umbrella valve, spring loaded ball valve, spring loaded poppet valve and rupturing disc. In some cases, the pressure relief valve is a two-way valve that allows for the passage of fluid in two directions when open.

Pressure relief valves may be made of any material suitable for integration within an indwelling medical device. Materials include, without limitation, silicone, elastomers, fluoropolymers, synthetic or natural rubbers, polyethylene, polypropylene, nylon, acetal, PVDF, ABS, and hydrocarbon-resistant fluorosilicone rubber. Elastomeric materials are often characterized with a hardness of less than Shore A 75, less than Shore A 60, or preferably, less than Shore A 50. In some embodiments, a pressure relief valve is not ferromagnetic. In some cases, ferromagnetic valves are not used to allow a patient using a valve system within an indwelling medical device to be scanned by magnetic resonance imaging.

In some embodiments, a pressure relief valve is mechanically held within a valve system, for example, the valve is positioned on a seat. In some embodiments, a pressure relief valve is glued or otherwise held within a valve system. In other embodiments, a pressure relief valve is welded to another component of a valve system.

In some embodiments, a pressure relief valve is an umbrella valve, in exemplary embodiments, the umbrella valve comprises a diaphragm shaped sealing disk, i.e., umbrella shape, and a stem. When mounted in a seat the convex diaphragm flattens out against the valve seat and absorbs a certain amount of seat irregularities and creates a certain sealing force. The umbrella valve will allow forward flow once the head pressure creates enough force to lift the convex diaphragm from the seat and so it will allow flow at a predetermined pressure in one way and prevent back flow immediately in the opposite way. In some embodiments, the opening pressure is variable by varying seat thickness. In some cases, the stem height is from about 1 mm to about 20 mm, or about 1, 2, 3, 4, 5, 6, 7, 8, 9, 10, 11, 12, 13, 14, 15, 16, 17, 18, 19 or 20 mm. In some cases, the valve seat height is at least about 1, 2, 3, 4, or 5 mm. In some cases, the sealing disk has a diameter from about 5 mm to about 20 mm.

The cracking pressure of an umbrella valve may vary according to the configuration of the valve and/or the valve seat. In some embodiments, the height of a valve seat contributes to the cracking pressure of a valve residing in the seat. In some embodiments, the size of a vent in the valve seat contributes to a cracking pressure of the valve. For instance, for a valve requiring a high flow rate, the flow vents in the seat are larger and for a valve requiring a low flow rate, the flow vents in the seat are smaller. In some cases, for a valve that requires resistance to high backpressure, the flow vents in the seat are smaller, the seat is taller and the umbrella is more substantial such that the edge of the umbrella would be more difficult to lift up. In some cases, for a valve that requites resistance to low backpressure, the flow vents in the seat are wider, the seat is thinner, and the umbrella is less substantial such that the edge of the umbrella would be easier to lift up. In some embodiments, a valve seat is selected for a valve system herein having a thickness of about 0.5 mm to about 5 mm, about 0.5 mm to about 4 mm, about 0.5 mm to about 3 mm, about 0.5 mm to about 2 mm, about 0.5 mm to about 1 mm, about 1 mm to about 5 mm, about 1 mm to about 4 mm, about 1 mm to about 3 mm, or about 1 mm to about 2 mm. In some embodiments, a valve seat has a seat height of about 0.5, 0.6, 0.7, 0.8, 0.9, 1, 1.1, 1.2, 1.3, 1.4, 1.5, 1.6, 1.7, 1.8, 1.9, 2, or 2.5 mm. The cracking pressure of the umbrella valve may be from about 30 mm Hg to about 90 mm Hg, or from about 50 mm Hg to about 70 mm Hg.

In some embodiments, an umbrella valve is a Belleville valve comprising a stem that is held in place in a seat by a retainer Hus retainer could be a separate component or an integral part of the device in which it is integrated such as a cap or lid just above the umbrella valve. In some embodiments, a pressure relief valve is a duckbill valve. In exemplary embodiments, the duckbill valve comprises elastomeric lips in the shape of a duckbill which prevent backflow and allow forward flow. Duckbill valves may not require integration with a seat surface to form a seal. Instead, the sealing function of the valve is an integral component of the valve.

In some embodiments, a pressure relief valve is a split valve. In some embodiments, a split valve comprises a distal slit partially across a transverse valve section, wherein the slit is configured to be open by receipt of a force pushed against one side of the valve, and then closed when the force is removed. For example, the force is the pressure exerted by fluid within the valve system during inflation. As another example, the force is the pressure within the valve system caused by application of another external force on an inflatable portion of an inflatable indwelling medical device. In some cases, the valve seal comprises two opposing halves, either molded separately or formed from an integrally molded valve seal that is bisected and then fused together to form a weak bond that is easily broken during splitting.

In some embodiments, a pressure relief valve is a cartridge type in which a rigid seating is incorporated. In some cases, a cartridge type valve typically comprises a body. O-ring, poppet, cartridge and a metal spring. In some cases, a cartridge type valve comprises a body, O-ring, and an umbrella valve. In some cases, a cartridge type valve comprises a body, O-ring, and a duckbill valve.

In some embodiments, a pressure relief valve is a film valve or cracking pressure check valve. In some embodiments, a pressure relief valve is an umbrella valve. A cracking pressure check valve comprises multiple components that are integrated into a single, molded valve. By changing the tension on the valve stem, a different cracking pressure can be achieved. The flow rate is controlled by varying the size of the valve orifices.

In some embodiments, a pressure relief valve is a spring loaded ball valve that releases fluid when its cracking pressure is reached, and then closes when the pressure drops below the cracking pressure. The spring loaded ball valve may comprise a ball positioned against a spring such that when the cracking pressure is reached, the pressure exerts a force on the ball that compresses the spring to allow the fluid to move in a forward direction. The cracking pressure of the spring loaded ball valve may be from about 30 mm Hg to about 90 mm Hg, or from about 50 mm Hg to about 70 mm Hg.

In some embodiments, a pressure relief valve is a spring loaded poppet valve positioned within the valve system such that the spring of the poppet valve and the pressure from within the second passage apply opposing forces on the spring loaded poppet valve. When the force from the second passage exerts a greater force than the spring force (i.e. the cracking pressure), then the poppet moves away from a valve seat, allowing fluid to pass through an outlet port of the spring loaded poppet valve. As the pressure within the second passage drops below the cracking pressure of the valve, the valve closes. The cracking pressure of the spring loaded poppet valve may be from about 30 mm Hg to about 90 mm Hg, or from about 50 mm Hg to about 70 mm Hg.

Fill Indicator

In some embodiments, a valve system comprises, or is operably connected to, a fill indicator that indicates to a clinician and/or user once an inflatable portion has reached and/or exceeded an optimal fill volume; an optimal fill pressure; or either an optimal fill volume or optimal fill pressure, whichever is reached first. The fill indicator may reside within the body of the valve system or be a separate component from the body. If the system comprises a return fluid path and an enclosure (e.g., return lumen), the fill indicator may reside within the enclosure. In some instances, the fill indicator resides within the body of a valve system in fluid communication with a return fluid path. In some embodiments, a fill indicator is a visual and/or audible indicator that provides notification once an inflatable portion has reached or surpassed an optimal fill volume and/or pressure. In some cases, a fill indicator is a mechanical element configured to alternate between a first physical state and a second physical state depending on a pressure within the second passage corresponding to the pressure within the inflatable portion. As a non limiting example, the mechanical element is in a first physical state when the optimal fill volume and/or pressure within the inflation portion has not been met, and in a second physical state when the optimal fill volume and/or pressure has been met or exceeded. In some cases, the mechanical element is in a first physical state when the inflatable portion is under-inflated. In some cases, the mechanical element is in a second physical state when the inflatable portion is over-inflated. In various embodiments, the mechanical element is in a second physical state when the inflatable portion is filled to an optimal fill volume and/or pressure.

In some embodiments, a valve system comprises both a fill indicator and a pressure relief valve, such that the fill indicator indicates when a first pressure is achieved and the pressure relief valve prevents over-inflation when a second pressure is achieved. In some cases, the pressure relief valve prevents over-inflation by opening once the second pressure is reached. In some cases, the second pressure is a predetermined fill pressure corresponding to the cracking pressure of the pressure relief valve. In some cases, the second pressure is a maximum fill pressure. In some cases, the first pressure is an optimal fill pressure. In some cases, the pressure relief valve prevents over-inflation by not allowing the inflatable portion to reach a pressure higher than the first pressure. In some cases, the pressure relief valve prevents over-inflation by not allowing the inflatable portion to reach a pressure higher than a desirable pressure, which is higher than the optimal fill pressure, and is defined by the pressure that could cause significant tissue damage over an extended period of tissue contact. In some cases, the pressure relief valve prevents over-inflation by not allowing the inflatable portion to reach a pressure that is 5%, 10%, 15%, 20%, 25%, 30%, 50%, or 100% higher than the first pressure. In some cases, the first pressure is different from the second pressure. In some cases, the first pressure is lower than the second pressure. In some cases, the first and second pressures differ by less than about 100%, 75%, 50%, 40%, 30%, 20%, 15%, 10%, 5%, or 1%.

Inflatable Indwelling Medical Devices

The valves and valve systems provided herein are useful for controlling the pressure within inflatable portions of indwelling medical devices. In some cases, the medical device comprises a rectal catheter. In some cases, the medical device comprises a urinary catheter in some cases, the medical device comprises an airway catheter. In some cases, the medical device comprises a tracheal catheter. In some embodiments, the inflatable portion is a retention balloon configured to retain a distal end of device within a body cavity. In some cases, an inflatable portion, e.g., retention balloon, has a fill capacity less than about 70 ml, 60 ml, 50 ml, 45 ml, 40 ml, 35 ml, 30 ml, 25 ml, 20 ml, 15 ml, 10 ml or less. In some cases, the inflatable portion is a retention balloon of a fecal management system comprising a rectal catheter and has a fill capacity from about 25 ml, to about 60 ml, from about 25 ml to about 50 ml, from about 35 ml to about 45 ml, from about 30 ml to about 60 ml, from about 30 ml to about 50 ml, from about 30 ml to about 45 ml, from about 35 ml to about, 55 ml, from about 35 ml to about 50 ml, from about 35 ml to about 45 ml, or from about 40 ml to about 50 ml. In some cases, the inflatable portion inflates with no more than about 55, 54, 53, 52, 51, 50, 49, 48, 47, 46, 45, 44, 43, 42, 41 or 40 mL of liquid. In some cases, the inflatable portion inflates with no more than about 45 mL of liquid. In such cases where the inflatable portion is inflated with no more than 45 mL of liquid, the pressure within the inflatable portion may be about 50 mm Hg±5 mm Hg when the pressure relief valve is triggered to open. In some cases, the inflatable portion inflates with no more than about 50 mL of liquid. In such cases where the inflatable portion is inflated with no more than 50 mL of liquid, the pressure within the inflatable portion may be about 50 mm Hg±5 mm Hg when the pressure relief valve is triggered to open. The pressure at which the pressure relief valve opens, the cracking pressure, may be tailored to each patient. As such, the range of cracking pressures for a pressure relief valve may be from about 50 mm Hg to about 70 mm Hg. This may allow for variation between patients and pressure relief valves.

In some cases, the inflatable portion is a retention balloon of a urinary catheter that has a fill capacity from about 5 ml to about 20 ml, from about 5 mi to about 15 ml, from about 8 ml to about 12 ml. In some embodiments, the inflatable portion comprises a foam filling. In some instances, the foam will self-inflate the inflatable portion. This enables the inflatable portion to return to its original size following a pressure change. For example, the pressure changes with a contraction and expansion cycle within the body, such as occurs during and following a cough. Suitable foams include polyurethane foams and memory foams.

In various aspects, a valve system described herein allows for an inflatable portion of an inflatable medical device to be filled with fluid to an optimal volume and/or pressure to prevent under-inflation or over-inflation of the inflatable portion. In some embodiments, the fluid is air. In some embodiments, the fluid is a liquid, for example, water or saline solution.

In some embodiments, an optimal fill pressure is a pressure between a minimum pressure and a maximum pressure within an inflatable portion of an inflatable indwelling medical device. In some cases, the minimum pressure corresponds to a minimum pressure necessary to retain the inflatable portion within a body cavity. In some cases, the maximum pressure is the highest amount of pressure an inflatable portion can handle before the inflatable portion is over-inflated. Over-inflation may result in abnormal blood perfusion in the soft tissue contacted by the inflatable portion, and/or pressure necrosis of the soft tissue. In some embodiments, an optimal fill pressure is from about 20 mm Hg to about 90 mm Hg, from about 20 mm Hg to about 80 mm Hg, from about 20 mm Hg to about 70 mm Hg, from about 20 mm Hg to about 60 mm Hg, from about 20 mm Hg to about 50 mm Hg, from about 30 mm Hg to about 90 mm Hg, from about 30 mm Hg to about 80 mm Hg, from about 30 mm Hg to about 70 mm Hg, or from about 30 mm Hg to about 50 mm Hg. In some cases, a minimum fill pressure is from about 20 mm Hg to about 50 mm Hg, for example, about 20, 25, 30, 35, 40, 45 or 50 mm Hg. In some cases, a maximum fill pressure is from about 40 to about 90 mm Hg, for example, about 40, 45, 50, 55, 60, 65, 70, 75, 80, 85, or 90 mm Hg. In some embodiments, a maximum pressure corresponds to the cracking pressure of a valve used within the system. In some embodiments, a maximum pressure corresponds to a pressure about 5%, 10%, 15%, 20%, 30%, 40%, or 50% greater than the cracking pressure of a valve used within the system. In some embodiments, a maximum pressure corresponds to the cracking pressure of a valve used within the system. In some embodiments, a preferred operation pressure corresponds to a pressure about 5%, 10%, 15%, 20%, 30%, 40%, or 50% lower than the cracking pressure of a pressure relief valve used within the system.

In some embodiments, an optimal fill volume is a volume between a minimum fill volume and a maximum fill volume. In some cases, wherein the valve system is part of an indwelling medical device, the minimum fill volume is the minimum volume of an inflatable portion necessary to retain the inflatable portion within a cavity of a patient. In some cases, the maximum fill volume is the maximum volume an inflatable portion can contain at a maximum pressure. In some cases, the optimal fill volume is patient dependent, for example, if the cavity of the patient is small or is under pressure (e.g., in obese patients), the optimal fill volume is lower than that of a patient with a larger cavity or a cavity that is not under said pressure. In some cases, the optimal fill volume for a retention balloon of an indwelling medical device is dependent on the characteristics of the body cavity, for example, the optimal fill volume for a urinary catheter system is smaller than that of a fecal catheter system. Non-limiting examples of minimum fill volumes for inflatable portions of rectal catheter systems include 5 ml, 10 ml, 20 ml, 25 ml, 26 ml, 27 ml, 28 ml, 29 ml, 30 ml, 31 ml, 32 ml, 33 ml, 34 ml, 35 ml, 40 ml, 45 ml, 50 ml, and 60 ml. Non-limiting examples of maximum fill volumes for inflatable portions of rectal catheter systems include 25 ml, 30 ml, 35 ml, 36 ml, 37 ml, 38 ml, 39 ml, 40 ml, 41 ml, 42 ml, 43 ml, 44 ml, 45 ml, 50 ml, 75 ml, and 100 ml. In some embodiments, an optimal fill volume for an inflatable portion of a rectal catheter system comprising a valve system described herein is from about 20 ml to about 50 ml, from about 30 ml to about 50 ml, from about 35 ml to about 45 ml, from about 30 ml to about 45 ml, and from about 35 ml to about 45 ml.

In various aspects of the valve systems provided herein, a pressure relief valve is configured to prevent over-inflation of an inflatable portion of an inflatable indwelling medical device past a predetermined fill volume. In some cases, the predetermined fill volume is the maximum fill volume or about 100%, 75%, 50%, 30%, 25%, 20%, 15%, 10%, 5% or 1% less than the maximum fill volume. In other cases, the predetermined fill volume is the optimal fill volume or about 5%, 10%, 15%, 20%, 25%, 50%, 75% greater than the optimal fill volume. In some embodiments, a valve of a valve system prevents the over-inflation of the inflatable portion past a predetermined fill pressure. In some cases, the predetermined fill pressure is the maximum fill pressure or about 100%, 75%, 50%, 30%, 25%, 20%, 15%, 10%, 5% or 1% less than the maximum fill pressure. In other cases, the predetermined fill pressure is the optimal fill pressure or about 5%, 10%, 15%, 20%, 25%, 50%, 75% greater than the optimal fill pressure. In some embodiments, a pressure relief valve prevents the inflation of the inflatable portion past either a predetermined fill volume or a predetermined fill pressure, whichever occurs first. As one example, the pressure relief valve prevents the over-inflation of the inflatable portion once it reaches a predetermined fill pressure, even if the predetermined fill volume has not been met. This may occur in catheter devices, wherein the size of the body cavity (e.g., rectal cavity, bladder) is smaller or under more pressure in some patients than in others.

In some cases, an indwelling medical device is a fecal catheter or a urinary catheter. Such a catheter comprises an inflation port, a balloon, a catheter tube, a drainable bag, a sample port, an irrigation port, etc. In some cases, the balloon is made from elastomers such as a silicone, natural rubber, or elastomers. In some cases, the catheter is made from silicone, natural rubber, or elastomers. In some cases, the inflation port comprises a Luer access check valve to allow for balloon inflation. Balloon materials include, without limitation, plastic, silicone, elastomers, fluoropolymers, synthetic or natural rubbers, polyethylene, polypropylene, nylon, acetal, PVDF, ABS, and hydrocarbon-resistant fluorosilicone rubber.

An inflatable indwelling medical device may comprise: (a) an apparatus composing a fluid inlet port and a fluid outlet port connected by a first passage, and a second passage, wherein the first passage and the second passage are not connected within the apparatus; (b) a retention balloon; (c) a supply fluid path connecting the first passage of the apparatus at the fluid outlet port to the retention balloon; (d) a return fluid path connecting the second passage to the retention balloon; wherein the second passage comprises a pressure relief valve that opens at a predetermined pressure. In some cases, the predetermined pressure is from about 30 mm Hg to about 90 mm Hg, or from about 50 mm Hg to about 70 mm Hg. In some cases, the inflatable indwelling medical device further comprises a fill indicator that provides notification when the retention balloon is filled to or above an optimal fill level. The fill indicator may be positioned at the second passage. The retention balloon may be positioned at the distal end of a catheter for insertion into a body cavity of a patient. The proximal end of the catheter may be configured for coupling to a collection bag. In some embodiments, the inflatable indwelling medical device is a fecal management system (FMS) and the catheter is a rectal catheter. In some embodiments, the inflatable indwelling medical device is a urinary management system and the catheter is a urinary catheter. In some embodiments, the retention balloon is configured for insertion within the body cavity so that when the balloon is inflated to a minimum volume and/or pressure, the inflated balloon maintains the distal end of the catheter within the body cavity, allowing for body waste to flow from the body cavity, through the drain channel of the catheter, and into the collection bag.

Methods of preventing over-inflation of a retention balloon of the indwelling medical device may comprise: (a) providing an indwelling medical device comprising (i) a tubular element defining a drain passage for effluent from a body cavity; (ii) a retention balloon located at a distal end of the tubular element for insertion into the body cavity; (iii) a housing comprising a pressure relief valve and an inflation port; (iv) an inflation lumen providing a First fluid path between the retention balloon and the housing, wherein the retention balloon is located at a distal end of the inflation lumen and the inflation port is located at a proximal end of the inflation lumen; and (v) a return lumen providing a second fluid path between the retention balloon and the housing, wherein the retention balloon is located at a distal end of the return lumen and the housing is located a proximal end of the return lumen, and wherein the valve is in fluid communication with the second fluid path; (b) inserting the retention balloon beyond an external orifice and into a body cavity; (c) connecting an attachment member comprising a fluid to the inflation port; (d) introducing the fluid into the retention balloon from the attachment member at a flow rate that is less than a cracking pressure of the valve until the retention balloon reaches an optimal fill volume; (e) disconnecting the attachment member; and (f) maintaining the filled retention balloon within the cavity for a defined period of time; wherein a pressure within the retention balloon is regulated by the valve.

EXAMPLES

Example 1

Fecal Management System Comprising a Valve System

A valve system is integrated within a fecal management system (FMS) to prevent over-inflation of the retention balloon of the FMS. The FMS has the configuration generally shown in FIG. 1. The FMS comprises a retention balloon 108 that is configured for placement within the rectal cavity to retain a catheter having a drain channel 102 for the diversion of waste fluids from the rectal cavity of a patient to a fluid collection bag. The FMS of this example further comprises an auxiliary lumen to provide irrigation to the rectal cavity.

Over-inflation of the retention balloon 108 is achieved by utilizing a valve system generally depicted by "B" in FIG. 1. The valve system B composes first passage connecting an inflation port 116 to an inflation lumen 110, which is further connected to the retention balloon 108. The inflation port 116 comprises an opening to allow for the passage of fluid between a syringe and the retention balloon 108 via a first fluid pathway comprising the first passage within the valve system B, and a supply fluid path within inflation lumen 110. The valve system B further comprises a second passage. A second fluid pathway connects the retention balloon 108, a return lumen 122, and the second passage. In this example, the second passage and the first passage do not interact. The second passage comprises a fill indicator that provides a notification, such as a visual notification, when an optimal pressure within the retention balloon 108 has been met. The second passage further comprises an umbrella valve having open and closed configurations. The umbrella valve opens when the pressure within the system reaches the cracking pressure of the valve, releasing pressure from within the system. The cracking pressure was selected to correspond to an over-inflation pressure within the retention balloon 108.

Example 2

Over-Inflation Control in a Fecal Management System Comprising a Valve System Equipped with a Pressure Relief Valve Set at 60 mm Hg Fill properties of retention balloons in a FMS as described in Example 1 were compared to the properties of retention balloons in a FMS lacking a pressure relief valves (control device).

A FMS as described in Example 1 was equipped with a pressure relief valve set at 60 mm Hg. A cartridge valve having an outside diameter of 10 mm with a 7 mm umbrella valve made from a Shore A 50 silicone was glued into the valve system. The height of the cartridge valve was 6 mm. The cartridge valve was made from ABS.

The retention balloons of the FMS with and without the pressure relief valves were filled with air from 5 cc up to 100 cc to observe the balloon diameter and the filled balloon pressure, respectively. The data was plotted as shown in FIGS. 6-9.

Figure 6:
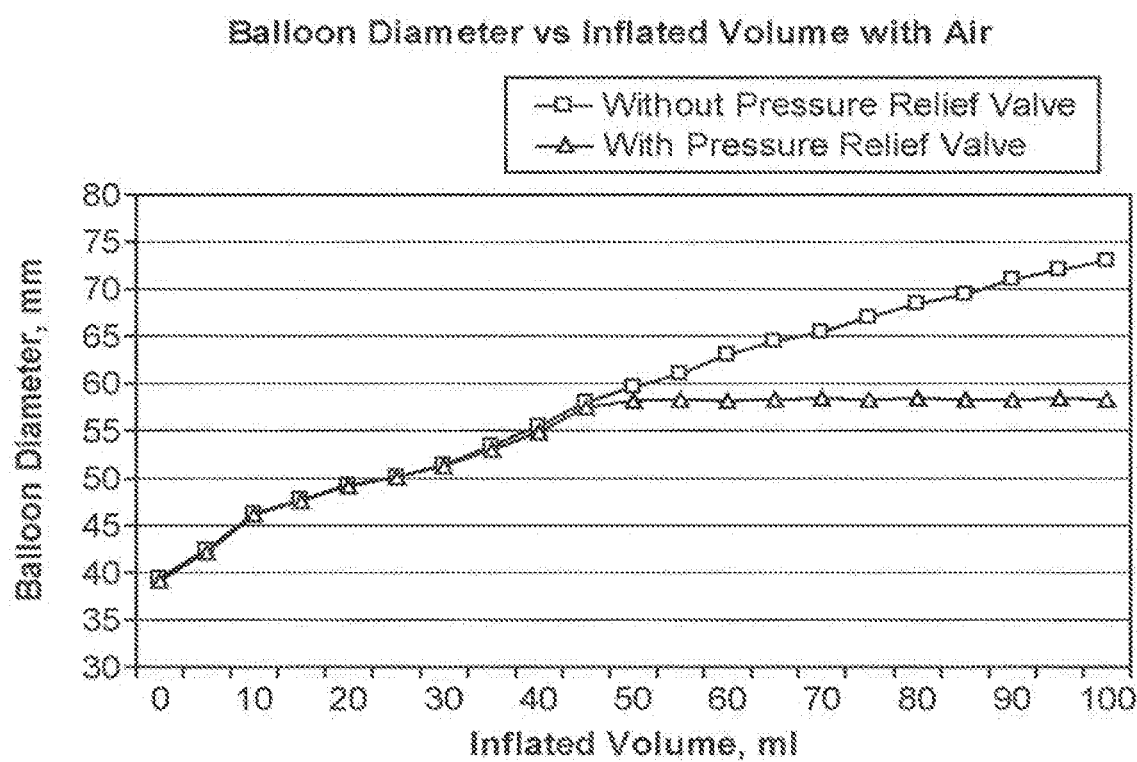
FIG. 6 is a plot of balloon diameter versus the inflated volume of the balloon when the balloon is inflated with air in a system having or not having a pressure relief valve.

As shown in FIG. 6, the balloon diameter expands linearly with the filled volume in the control device lacking the pressure relief valve. In the systems comprising the pressure relief valve, the balloon diameter expands linearly with the filled volume until it reaches at around 58.3 mm diameter, it then stays at around 58.3 mm upon further increase in fill volume.

Figure 7:
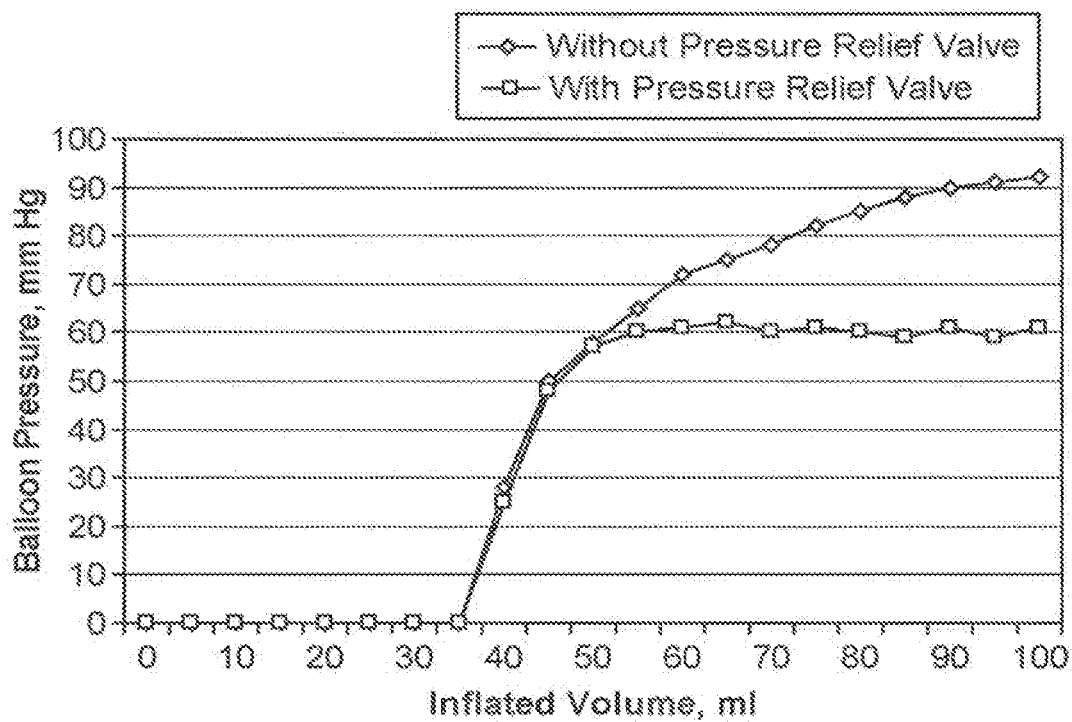
FIG. 7 is a plot of balloon pressure versus the inflated volume of the balloon when the balloon is inflated with air in a system having or not having a pressure relief valve.
Figure 8:
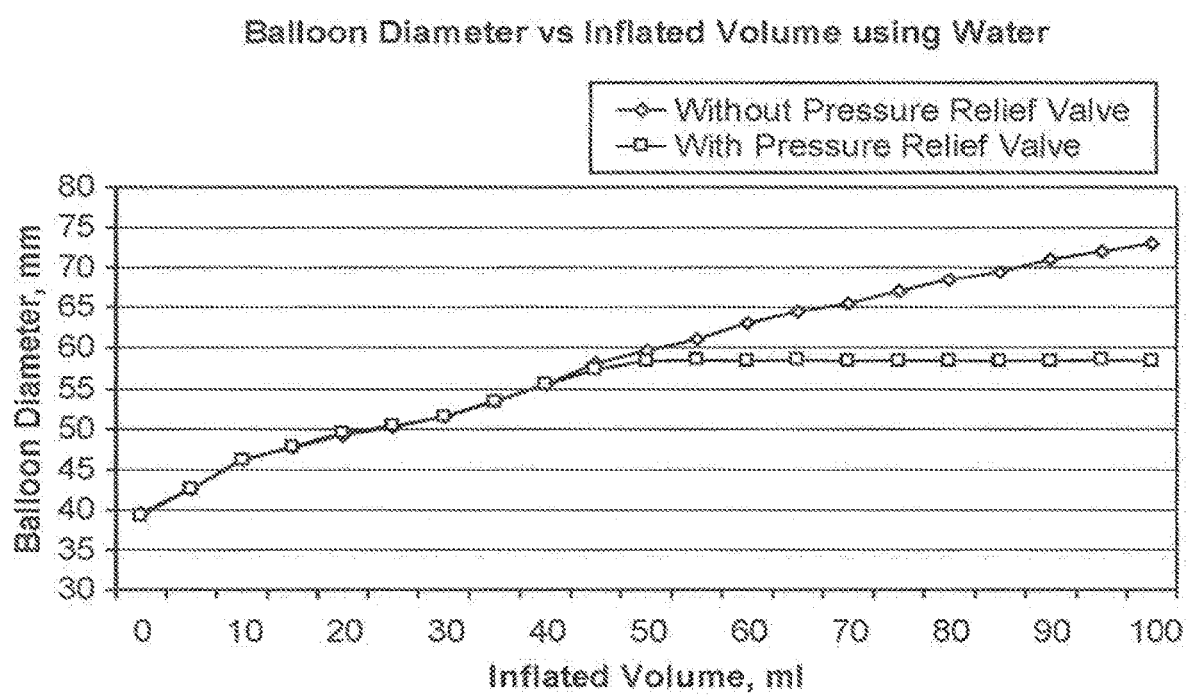
FIG. 8 is a plot of balloon diameter versus the inflated volume of the balloon when the balloon is inflated with water in a system having or not having a pressure relief valve.
Figure 9:
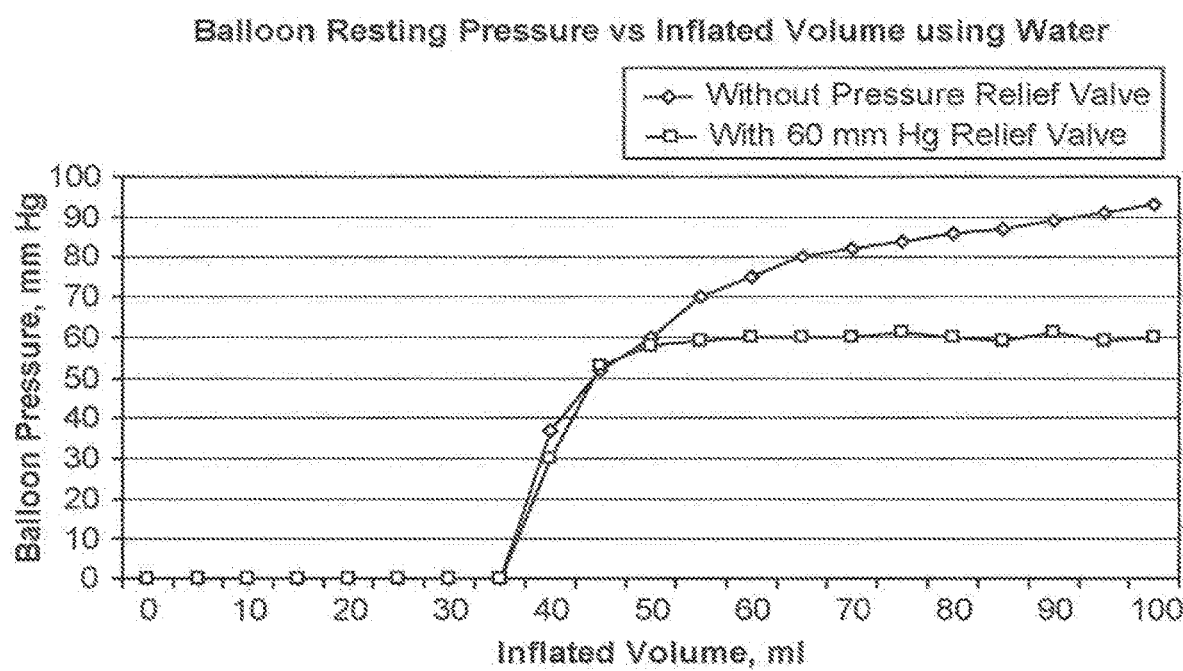
FIG. 9 is a plot of balloon pressure versus the inflated volume of the balloon when the balloon is inflated with water in a system having or not having a pressure relief valve.

The measurement of the balloon pressure versus the filled volume with air is shown in FIG. 7. The balloon pressure stayed near zero initially because the balloon was molded with a set diameter of around 51 mm. The balloon pressure began to rise exponentially at around 35 ml filled volume, and continued to rise to about 93 mm Hg in the control system. In the system comprising the pressure relief valve, the balloon pressure followed about the same trend as the control device at a filled volume from 0 ml to around 50 ml. After 50 ml, the balloon pressure stayed at around 60 mm Hg because of the control by the pressure relief valve. The same test was repeated with the water instead of air. The plots of FIG. 8 and FIG. 9 show that similar trends were observed as FIG. 6 and FIG. 4, respectively.

These experiments show that the system comprising the pressure relief valve was effective in shutting off the pressure above the cracking pressure of the valve at 60 mm Hg, while allowing the system to be functional above a 40 ml optimum filled volume, at which point the fill indicator dome would begin to indicate the onset of the balloon inflation.

Example 3

Over-Inflation Control in a Fecal Management System Comprising a Valve System Equipped with a Pressure Relief Valve Set at 75 mm Hg Fill properties of retention balloons in a FMS as described in Example 1 were compared to the properties of retention balloons in FMS without pressure relief valves (control device).

A FMS as described in Example 1 was equipped with a pressure relief valve set at 60 mm Hg (as in Example 2), 75 mm Hg, or no pressure relief valve (control device). In the 75 mm Hg system, the cartridge valve had an outside diameter of 10 mm with a 7 mm umbrella valve. The height of the cartridge was 6 mm. The cartridge valve was made from ABS. The cartridge valve was glued into the valve system of the FMS of Example 1.

The balloons of each system were filled with water from 5 cc up to 100 cc to observe the balloon pressure among three systems, respectively. The data was plotted as shown in FIG. 10. The balloon pressure stayed near zero initially since the balloon was molded with a set diameter of around 51 mm. The balloon pressure began to rise exponentially at around 35 ml filled volume, and then continue to rise to about 93 mm Hg in the control system. In the test system having the 60 mm Hg cracking pressure relief valve, the balloon pressure followed about the same trend as the control device at a filled volume from 0 ml to around 50 ml. After 50 ml, the balloon pressure stayed at around 60 mm Hg. In the system having a 75 mm Hg cracking pressure relief valve, the balloon pressure followed about the same trend as the control device at a filled volume from 0 ml to around 60 ml. After 60 ml, the balloon pressure stayed at around 75 mm Hg. This data show that the pressure relief valve systems were effective in shutting off the pressure above the cracking pressure of the valve (60 mm Hg or 75 mm Hg), while allowing the test device to be functional above 40 ml optimum filled volume, in which the fill indicator dome would begin to indicate the onset of the balloon inflation.

Example 4

Over-Inflation Control in a Fecal Management System Comprising a Spring Loaded Ball Valve System Equipped with a Critical Pressure Relief Set at 75 mm Hg An FMS as described in Example 1 was equipped with a spring loaded ball valve having a critical relief pressure set at 75 mm Hg. The spring loaded ball valve was purchased from Lee Co. (Westbrook, Conn., USA). The pressure relief valve has a diameter of 5.46 mm and a length of 7.3 mm. The ball valve was built from ceramic with a stainless steel housing, a stainless steel cage, and stainless steel spring. The critical relief pressure was controlled by the selection of the spring. The spring loaded ball valve was glued into the fill indicator of the FMS (Example 1), and is shown in FIGS. 3A and 3B.

The balloons of each system were filled with water from 5 cc up to 100 cc to observe the balloon pressure. The data generated was similar to the plot in FIG. 10 in that the pressure relief valve systems were effective in shutting off the pressure above the cracking pressure of the valve (75 mm Hg), while allowing the test device to be functional above 40 ml optimum filled volume, in which the fill indicator dome would begin to indicate the onset of the balloon inflation.

Example 5

Figure 4B:
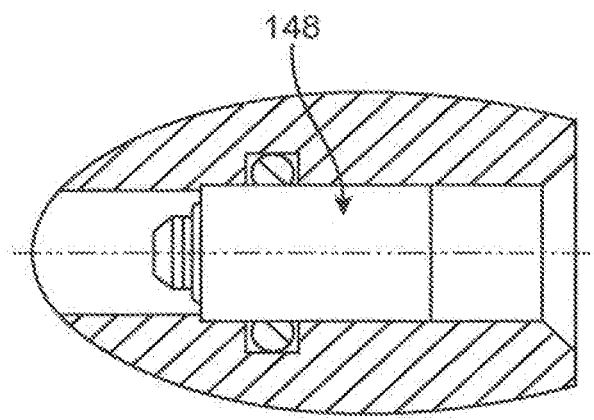
FIG. 4B is an embodiment of a spring loaded poppet valve for use in a valve system provided herein.

Over-Inflation Control in a Fecal Management System Comprising a Spring Loaded Poppet Valve System Equipped with a Critical Pressure Relief Set at 75 mm Hg An FMS as described in Example 1 was equipped with a spring loaded poppet valve having a critical relief pressure set at 75 mm Hg. The spring loaded poppet valve was purchased from Check Valve, Inc. (Maplewood, Minn., USA). The pressure relief valve has a diameter of 6.35 mm (¼") and a length of 12.2 mm. The poppet valve was built from nylon. The spring loaded poppet valve was glued into the fill indicator of the FMS (Example 1), and is shown in FIGS. 4A and 4B.

The balloons of each system wore filled with water from 5 cc up to 100 cc to observe the balloon pressure. The data was similar to the plot in FIG. 10 in that the pressure relief valve systems were effective in shutting off the pressure above the cracking pressure of the valve (75 mm Hg), while allowing the test device to be functional above 40 ml optimum filled volume, in which the fill indicator dome would begin to indicate the onset of the balloon inflation. Due to the height of poppet valve, the profile of the mounted pressure relief valve is slightly higher than the spring loaded ball valve in Example 4.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the inventions described herein may be employed in practicing the inventions. It is intended that the following claims define a scope of the inventions and that methods and structures within the scope of these claims and their equivalents be covered thereby.

What is claimed is:

1. A method of filling an inflatable portion of a device to a predetermined operating range, the method comprising:
   a) providing the device comprising the inflatable portion, the inflatable portion being in fluid communication with
      i. an inflation port via an inlet passage, and
      ii. a fill indicator and a pressure relief valve in a closed configuration, via an outlet passage;
      wherein the inflatable portion has a minimum operating fill volume and a maximum operating fill volume, and a fill volume between and including the minimum and maximum operating fill volumes is the predetermined operating range of the inflatable portion; and
      wherein the inlet passage and the outlet passage are enclosed within an apparatus, and the inlet passage and the outlet passage are not in fluid communication within the apparatus;
   b) providing a fluid to the inflatable portion through the inflation port and the inlet passage to fill the inflatable portion until the fill indicator indicates that the minimum operating fill volume is achieved.

2. The method of claim 1, wherein the pressure relief valve opens at a cracking pressure from 30 mm Hg to 90 mm Hg.

3. The method of claim 1, wherein the inflatable portion is inserted into a cavity of a subject.

4. The method of claim 3, wherein the pre-determined operating range of the inflatable portion is determined by the identity and/or dimensions of the cavity of the subject.

5. The method of claim 4, further comprising selecting a cracking pressure of the pressure relief valve depending on the cavity of the subject.

6. The method of claim 1, wherein the minimum operating fill volume is from 30 ml to 45 ml.

7. The method of claim 1, wherein the maximum operating fill volume is from 45 ml to 70 ml.

8. The method of claim 1, wherein the pressure relief valve is positioned on a valve seat, and wherein a cracking pressure of the pressure relief valve is dependent on the height of the valve seat.

9. The method of claim 1, wherein the pressure relief valve comprises an umbrella valve, spring loaded ball valve, spring loaded poppet valve, rupturing disk, or a combination thereof.

10. The method of claim 1, wherein the pressure relief valve has a height no greater than 20 mm.

11. The method of claim 1, wherein the fill indicator is a pressure indicator comprising a mechanical element configured to alternate between a first physical state and a second physical state when a pressure within the inflatable portion meets or exceeds the minimum operating fill volume.

12. The method of claim 1, further comprising:
   c) continuing to provide the fluid to the inflatable portion through the inflation port and the inlet passage until: (i) the pressure relief valve opens into an open configuration to restrict the inflation portion from being filled beyond the maximum operating fill volume, or ii) before the pressure relief valve opens into the open configuration.

13. The method of claim 1, wherein the fill indicator provides an indication when fluid pressure in the outlet passage exceeds a first predetermined pressure corresponding to the minimum operating fill volume; and
   wherein the pressure relief valve opens when fluid pressure in the outlet passage exceeds a second predetermined pressure corresponding to the maximum operating fill volume.

14. The method of claim 1, wherein the fill indicator comprises an electronic device that provides an audible alert and/or a visual alert to indicate that the minimum operating fill volume is achieved.

15. The method of claim 1, further comprising causing a breakable member to rupture in response to pressure in the apparatus exceeding a predetermined pressure; and
   wherein the predetermined pressure is greater than or equal to a cracking pressure of the pressure relief valve.

16. The method of claim 1, further comprising:
   after inflation of the inflatable member, opening the pressure relief valve in response to pressure within the inflatable portion exceeding a cracking pressure of the pressure relief valve.

17. The method of claim 1, wherein the inflatable portion is in continuous fluid communication with the pressure relief valve via the outlet passage.

18. The method of claim 17, wherein the inflatable portion is in continuous fluid communication with the pressure relief valve via the outlet passage before, during, and after filling of the inflatable portion.

19. A method of filling an inflatable portion of a device to a predetermined operating range, wherein the inflatable portion has a minimum operating fill volume and a maximum operating fill volume, and a fill volume between and including the minimum and maximum operating fill volumes is the predetermined operating range of the inflatable portion, the method comprising:
   placing the inflatable portion in fluid communication with an inlet passage including an inflation port;
   placing the inflatable portion in fluid communication with an outlet passage including a fill indicator and a pressure relief valve in a closed configuration;
   providing a fluid to the inflatable portion through the inflation port and the inlet passage to fill the inflatable portion until the fill indicator indicates that the minimum operating fill volume is achieved;
   wherein the inlet passage and the outlet passage are enclosed within an apparatus, and the inlet passage and the outlet passage are not in fluid communication within the apparatus.

20. The method of claim 19, further comprising:
   in response to a fluid pressure exceeding a first predetermined pressure, providing, by the fill indicator, an indication that the minimum operating fill volume has been achieved in the inflatable portion; and
   in response to the fluid pressure exceeding a second predetermined pressure greater than the first predetermined pressure, opening the pressure relief valve, thereby preventing the inflatable portion from exceeding the maximum operating fill volume.

21. The method of claim 20, further comprising selecting the first predetermined pressure based upon a cavity into which the inflatable portion will be inserted.

22. The method of claim 20, further comprising selecting the second predetermined pressure based upon a cavity into which the inflatable portion will be inserted.

23. The method of claim 19, further comprising selecting a cracking pressure of the pressure relief valve depending on a cavity into which the inflatable portion will be inserted.

24. The method of claim 19, wherein placing the inflatable portion in fluid communication with an outlet passage places the inflatable portion in continuous fluid communication with the fill indicator and the pressure relief valve.

\* \* \* \* \*